(12) United States Patent
Shimizu et al.

(10) Patent No.: US 11,014,868 B2
(45) Date of Patent: May 25, 2021

(54) METHOD FOR PRODUCING ACETIC ACID

(71) Applicant: DAICEL CORPORATION, Osaka (JP)

(72) Inventors: Masahiko Shimizu, Himeji (JP); Ryuji Saito, Ohtake (JP); Hiroyuki Miura, Himeji (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 15/510,148

(22) PCT Filed: Nov. 17, 2016

(86) PCT No.: PCT/JP2016/084116
§ 371 (c)(1),
(2) Date: Mar. 9, 2017

(87) PCT Pub. No.: WO2017/149856
PCT Pub. Date: Sep. 8, 2017

(65) Prior Publication Data
US 2017/0260120 A1    Sep. 14, 2017

(30) Foreign Application Priority Data

Mar. 1, 2016 (JP) .............................. JP2016-038582

(51) Int. Cl.
| C07C 51/38 | (2006.01) |
| C07C 51/087 | (2006.01) |
| C07C 51/12 | (2006.01) |
| C07C 51/44 | (2006.01) |

(52) U.S. Cl.
CPC ............ C07C 51/38 (2013.01); C07C 51/087 (2013.01); C07C 51/12 (2013.01); C07C 51/44 (2013.01)

(58) Field of Classification Search
None
See application file for complete search history.

(56) References Cited

U.S. PATENT DOCUMENTS

| 6,130,355 A | 10/2000 | Jones | |
| 8,017,802 B2 * | 9/2011 | Scates | ...................... C07C 51/12 |
| | | | 562/607 |
| 2006/0011462 A1 | 1/2006 | Horiguchi et al. | |
| 2008/0293966 A1 | 11/2008 | Scates et al. | |
| 2012/0012316 A1 | 1/2012 | Putzig | |
| 2012/0123160 A1 | 5/2012 | Barron et al. | |
| 2014/0187812 A1 * | 7/2014 | Wellman | ............... C07C 51/573 |
| | | | 562/607 |

FOREIGN PATENT DOCUMENTS

| DE | 2423079 A1 | 11/1975 |
| EP | 0 936 209 A1 | 8/1999 |
| JP | 48-30254 B1 | 9/1973 |
| JP | 53-65814 A | 6/1978 |
| JP | 11-315046 A | 11/1999 |
| JP | 2001-505199 A | 4/2001 |
| JP | 2004-131389 A | 4/2004 |
| JP | 2014-503491 A | 2/2014 |
| WO | WO 98/22420 A1 | 5/1998 |

OTHER PUBLICATIONS

PCT Notification Concerning Documents Transmitted for International Application No. PCT/JP2016/084116 dated Jun. 7, 2017.
Written Opinion of the International Searching Authority for Application No. PCT/JP2016/084116 dated Feb. 21, 2017.
International Search Report for PCT/JP2016/084116 (PCT/ISA/210) dated Feb. 21, 2017.
Knopp et al., "The Thermodynamics of the Thermal Decomposition of Acetic Acid in the Liquid Phase", The Journal of Physical Chemistry, vol. 66, No. 8, 1962, pp. 1513-1516.
Extended European Search Report, dated Nov. 17, 2017, for European Application No. 16845319.9.
Japanese Office Action, dated Feb. 6, 2018, for Japanese Application No. 2017-515998, along with an English translation.
Japanese Decision of Refusal for Application No. 2017-515998, dated Sep. 11, 2018, with English language translation.
Extended European Search Report, dated Dec. 3, 2019, for European Application No. 19207190.0.
Bai et al., "Theoretical Study on Hydrolysis Mechanism of Acetic Anhydride," Journal of Dezhou University. vol. 27, No. 2, Apr. 2011, 15 pages total with an English translation.
Chinese Office Action and Search Report for Chinese Application No. 201680074162.7, dated Jan. 21, 2021.
Liu, "Study on Factors Affecting Acetic Anhydride Hydrolysis," Basic Organic Chemical Industry, vol. 35, No. 6, Jun. 2012. 5 pages total, with an English transation.

* cited by examiner

*Primary Examiner* — Ana Z Muresan
(74) *Attorney, Agent, or Firm* — Birch, Stewart, Kolasch & Birch, LLP

(57) ABSTRACT

A method for producing acetic acid includes subjecting an acetic acid solution to an acetic anhydride decreasing treatment. The acetic acid solution is present typically in, or downstream from, a distillation column (5) of acetic acid production equipment (X), includes acetic acid in a concentration of 90 mass percent or more, acetic anhydride, and water, and is in such a state that an equilibrium concentration of acetic anhydride is higher than an acetic anhydride concentration. The acetic anhydride decreasing treatment includes at least one of water concentration increasing and temperature lowering so as to bring the acetic acid solution into such a state that the equilibrium concentration of acetic anhydride is lower than the acetic anhydride concentration. The acetic acid production method is suitable for yielding a high-purity acetic acid product.

18 Claims, 1 Drawing Sheet

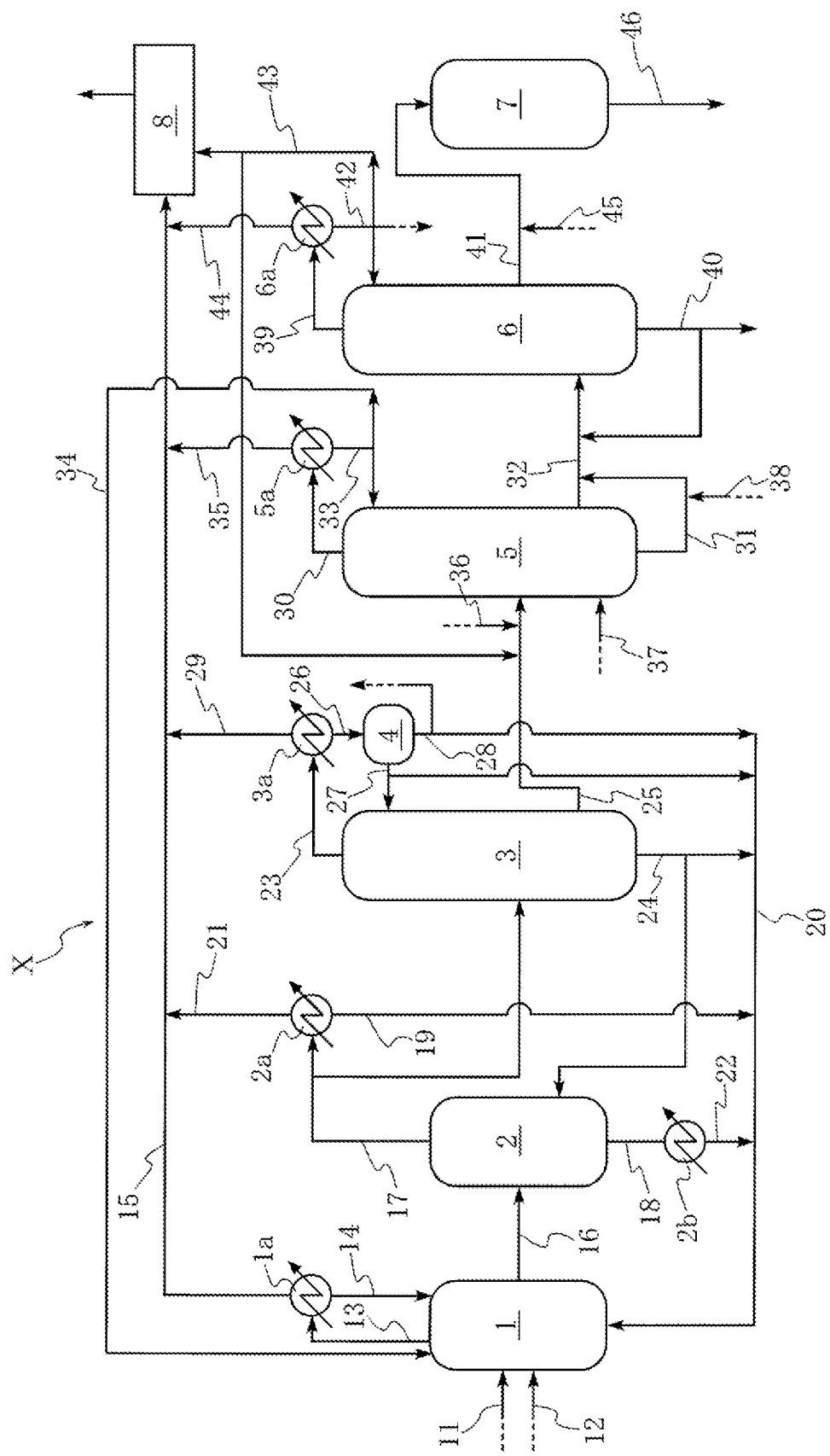

METHOD FOR PRODUCING ACETIC ACID

TECHNICAL FIELD

The present invention generally relates to methods for producing acetic acid. This application claims priority to Japanese Patent Application No. 2016-038582, filed Mar. 1, 2016, the entire contents of which application are incorporated herein by reference.

BACKGROUND ART

A methanol carbonylation process is known as an example of acetic acid synthesizing processes suitable for acetic acid industrial production. With this synthesizing process, starting materials methanol and carbon monoxide are brought to react with each other in the presence of a predetermined catalyst to form acetic acid.

An acetic acid production plant for use in acetic acid production using the methanol carbonylation process includes units such as a reactor, a flash evaporator, a low-boiling component removing column, and a dehydration column. In the acetic acid production plant as mentioned above, acetic acid is produced typically through processes in the individual units as follows. In the reactor, acetic acid is continuously formed from starting materials methanol and carbon monoxide by a methanol carbonylation reaction. In the flash evaporator, a reaction liquid from the reactor, where the reaction liquid contains acetic acid formed in the reactor, is subjected to a so-called flash evaporation treatment to extract vapor of crude acetic acid from the reaction liquid. In the low-boiling component removing column, the crude acetic acid is distilled, and a liquid acetic acid stream enriched with acetic acid is drawn out of the low-boiling component removing column. The distillation is performed mainly for removing low-boiling components from the crude acetic acid, where the low-boiling components have lower boiling points as compared with acetic acid. In the dehydration column, the acetic acid stream is distilled mainly for removing water from the acetic acid stream, and a liquid acetic acid stream further enriched with acetic acid is drawn out of the dehydration column. The acetic acid production technique as mentioned above is described typically in Patent Literature (PTL) 1 and PTL 2.

CITATION LIST

Patent Literature

PTL 1: Japanese Unexamined Patent Application Publication (JP-A) No. H11-315046
PTL 2: Japanese Unexamined Patent Application Publication (Translation of PCT Application) (JP-A) No. 2001-505199

SUMMARY OF INVENTION

Technical Problem

In acetic acid production typically using the carbonylation process as mentioned above, the resulting acetic acid product may contain acetic anhydride. The acetic anhydride concentration in the acetic acid product is preferably minimized for higher purity of the acetic acid product. The present invention has been made under these circumstances and has an object to provide a method for producing acetic acid, which method is suitable for obtaining a high-purity acetic acid product.

Solution to Problem

The present invention provides, in a first aspect, a method for producing acetic acid. The method includes an acetic anhydride decreasing treatment in the course of yielding an acetic acid product. The acetic anhydride decreasing treatment is performed on an acetic acid solution containing acetic acid in a concentration of 90 mass percent or more, acetic anhydride, and water and being in such a state that the equilibrium concentration of acetic anhydride is higher than the acetic anhydride concentration. The acetic anhydride decreasing treatment in the first aspect is the treatment of subjecting the acetic acid solution to at least one of water concentration increasing and temperature lowering to bring the acetic acid solution into such a state that the equilibrium concentration of acetic anhydride is lower than the acetic anhydride concentration. As used herein, the term "equilibrium concentration of acetic anhydride" refers to the acetic anhydride concentration of an acetic acid solution when an acetic anhydride hydrolysis reaction (i.e., a reaction of acetic anhydride and water to form acetic acid) and a reverse reaction thereof reach an equilibrium state in the acetic acid solution under a temperature condition and a pressure condition in which the acetic acid solution is present. The acetic anhydride hydrolysis reaction is an exothermic reaction, and the reverse reaction is an endothermic reaction.

In the acetic anhydride decreasing treatment in this method, the acetic acid solution having an acetic acid concentration of 90 mass percent or more and being in such a state that the equilibrium concentration of acetic anhydride is higher than the acetic anhydride concentration is subjected to water concentration increasing, or temperature lowering, or both (both water concentration increasing and temperature lowering in combination). The acetic anhydride decreasing treatment, when performed on the high-concentration acetic acid solution, brings the acetic acid solution into such a state that the equilibrium concentration of acetic anhydride is lower than the acetic anhydride concentration. In the resulting acetic acid solution brought into this state, an acetic anhydride hydrolysis reaction proceeds so that the acetic anhydride concentration in the solution decreases toward or to the equilibrium concentration of acetic anhydride. The method, which includes the acetic anhydride decreasing treatment in the course of yielding an acetic acid product, is suitable for decreasing the acetic anhydride concentration in the obtained acetic acid solution or in the acetic acid product and is therefore suitable for yielding such a high-purity acetic acid product.

The present invention also provides, in a second aspect, a method for producing acetic acid. The method includes an acetic anhydride decreasing treatment in the course of yielding an acetic acid product. The acetic anhydride decreasing treatment is performed on an acetic acid solution containing acetic acid in a concentration of 90 mass percent or more, acetic anhydride, and water and being in such a state that the equilibrium concentration of acetic anhydride is lower than the acetic anhydride concentration. The acetic anhydride decreasing treatment in the second aspect is the treatment of subjecting the acetic acid solution to at least one of water concentration increasing and temperature lowering to further lower the equilibrium concentration of acetic anhydride.

In the acetic anhydride decreasing treatment in this method, the acetic acid solution having an acetic acid concentration of 90 mass percent or more and being in such a state that the equilibrium concentration of acetic anhydride is lower than the acetic anhydride concentration is subjected to water concentration increasing, or temperature lowering, or both in combination. The acetic anhydride decreasing treatment as above, when performed on the high-concentration acetic acid solution, brings the acetic acid solution into such a state that the equilibrium concentration of acetic anhydride is further lowered. In the resulting acetic acid solution brought into this state, the acetic anhydride hydrolysis reaction tends to proceed so that the acetic anhydride concentration in the solution decreases toward or to the equilibrium concentration of acetic anhydride. The method, which includes the acetic anhydride decreasing treatment in the course of yielding an acetic acid product, is suitable for decreasing the acetic anhydride concentration in the obtained acetic acid solution or in the acetic acid product and is therefore suitable for yielding such a high-purity acetic acid product.

The present invention also provides, in a third aspect, a method for producing acetic acid. This method includes an acetic anhydride decreasing treatment in the course of yielding an acetic acid product. The acetic anhydride decreasing treatment is performed on an acetic acid solution containing acetic acid in a concentration of 90 mass percent or more, acetic anhydride, and water and being in such a state that the equilibrium concentration of acetic anhydride is lower than the acetic anhydride concentration. The acetic anhydride decreasing treatment in the third aspect is the treatment of subjecting the acetic acid solution to temperature rising alone or in combination with water concentration increasing, as long as the state is maintained, so as to perform acetic anhydride hydrolysis at a higher reaction rate.

In the acetic anhydride decreasing treatment in this method, the acetic acid solution having an acetic acid concentration of 90 mass percent or more and being in such a state that the equilibrium concentration of acetic anhydride is lower than the acetic anhydride concentration is subjected to temperature rising alone or in combination with water concentration increasing, while the state is maintained. The temperature rising alone or in combination with water concentration increasing on the acetic acid solution kinetically advantageously acts on increase in reaction rate of acetic anhydride hydrolysis. The acetic anhydride decreasing treatment, when performed on such a high-concentration acetic acid solution, increases the reaction rate of acetic anhydride hydrolysis while the state is maintained that the equilibrium concentration of acetic anhydride is lower than the acetic anhydride concentration. This promotes the acetic anhydride hydrolysis reaction so that the acetic anhydride concentration in the solution decreases toward or to the equilibrium concentration of acetic anhydride. This method, which includes the acetic anhydride decreasing treatment in the course of yielding an acetic acid product, is suitable for decreasing the acetic anhydride concentration in the obtained acetic acid solution or acetic acid product and is therefore suitable for yielding such a high-purity acetic acid product.

In the acetic anhydride decreasing treatments in the first, second, and third aspects of the present invention, a catalyst capable of functionally promoting acetic anhydride hydrolysis is preferably present in the acetic acid solution. The catalyst preferably includes at least one substance selected from Broensted acids, Lewis acids, corrodible metals, ion exchange resins, and sulfonic acids. The catalyst in the acetic acid solution may be present in an amount of preferably 0.01 to 10000 ppm. As used herein, the term "ppm" refers to "part by mass per million" (ppm by mass). These configurations are advantageous for allowing the acetic anhydride hydrolysis reaction to proceed and for thereby decreasing the acetic anhydride concentration in the acetic acid solution.

With the acetic anhydride decreasing treatments in the first, second, and third aspects of the present invention, the acetic acid solution may have a water concentration of typically 7 ppm or more and may have a temperature of typically 17° C. or higher. In preferred embodiments, the acetic acid solution in the acetic anhydride decreasing treatments in the first, second, and third aspects may be controlled to have a water concentration of 2000 ppm or more and a temperature of 180° C. or lower, or to have a water concentration of 1000 ppm or more and a temperature of 170° C. or lower, or to have a water concentration of 500 ppm or more and a temperature of 120° C. or lower, or to have a water concentration of 200 ppm or more and a temperature of 100° C. or lower, or to have a water concentration of 80 ppm or more and a temperature of 60° C. or lower, or to have a water concentration of 40 ppm or more and a temperature of 50° C. or lower, or to have a water concentration of 12 ppm or more and a temperature of 30° C. or lower. These configurations are advantageous for allowing the acetic anhydride hydrolysis reaction to proceed and for thereby decreasing the acetic anhydride concentration in the acetic acid solution.

The acetic acid solution after the acetic anhydride decreasing treatments in the first, second, and third aspects of the present invention may be held for a residence time of typically 1 second or longer, preferably 30 seconds or longer, more preferably 1 minute or longer, more preferably 5 minutes or longer, more preferably 10 minutes or longer, more preferably 30 minutes or longer, more preferably 60 minutes or longer, more preferably 900 minutes or longer, more preferably 1300 minutes or longer, more preferably 1400 minutes or longer, and more preferably 2800 minutes or longer. As used herein, the term "residence time" of the acetic acid solution after any of the acetic anhydride decreasing treatments refers to a period of time of holding the acetic acid solution typically in a pipe, in a distillation column, in a buffer tank, and/or in a product tank in the acetic acid production equipment, so as to enhance decrease in the acetic anhydride concentration in the acetic acid solution, where the decrease is caused by the treatment. These configurations are advantageous for allowing the acetic anhydride hydrolysis reaction to proceed and for thereby decreasing the acetic anhydride concentration in the acetic acid solution.

The acetic acid production methods according to the first, second, and third aspects of the present invention preferably further include a reaction step, a first distillation step, a second distillation step, and a third distillation step and are performed using acetic acid production equipment including a reactor, a first distillation column, a second distillation column, and a third distillation column. In the reaction step, a material mixture containing methanol and carbon monoxide is subjected to a methanol carbonylation reaction in the reactor to form acetic acid. In the first distillation step, a crude acetic acid stream containing the acetic acid formed in the reaction step is subjected to distillation in the first distillation column to give a first acetic acid stream, where the first acetic acid stream is enriched with acetic acid as compared with the crude acetic acid stream. In the second distillation step, the first acetic acid stream is subjected to distillation in the second distillation column to give a second acetic acid stream, where the second acetic acid stream is enriched with acetic acid as compared with the first acetic acid stream. In the third distillation step, the second acetic acid stream is subjected to distillation in the third distillation column to give a third acetic acid stream, where the third acetic acid stream is enriched with acetic acid as compared with the second acetic acid stream. An acetic acid stream present in or downstream from the second distillation column in the acetic acid production equipment is subjected, as the acetic acid solution, to any of the acetic anhydride decreasing treatments.

The acetic acid production equipment with which any of the methods is performed includes a reactor, a first distillation column, a second distillation column disposed downstream from the first distillation column, and a third distillation column disposed downstream from the second distillation column. In an embodiment, the acetic acid production equipment may further include a flash evaporator disposed between the reactor and the first distillation column. In another embodiment, the acetic acid production equipment may further include a product tank for storing a produced acetic acid product. In the methods, an acetic acid stream present in or downstream from the second distillation column in the acetic acid production equipment is subjected to any of the acetic anhydride decreasing treatments according to the first, second, and third aspects of the present invention. The methods, which include an additional distillation in the third distillation column in addition to distillation in the first and second distillation columns, are suitable for enabling high purity of the resulting acetic acid product. The acetic anhydride concentration in an acetic acid stream passing through the equipment may vary depending on the temperature condition and the pressure condition under which the acetic acid stream is present, and on the composition (formulation) of the acetic acid stream. According to the methods, an acetic acid stream or acetic acid solution present in or downstream from the second distillation column and which has been purified to a relatively high degree is subjected to any of the acetic anhydride decreasing treatments. The configurations are suitable for decreasing the acetic anhydride concentration in the resulting acetic acid product and is therefore suitable for yielding such a high-purity acetic acid product.

BRIEF DESCRIPTION OF DRAWINGS

The single FIGURE (FIG. 1) schematically illustrates the general arrangement of acetic acid production equipment with which an acetic acid production method according to an embodiment of the present invention is performed.

DESCRIPTION OF EMBODIMENTS

FIG. 1 schematically illustrates the general arrangement of an acetic acid production equipment X with which an acetic acid production method according to an embodiment of the present invention is performed. The acetic acid production equipment X includes a reactor 1, an evaporator 2, a distillation column 3, a decanter 4, a distillation column 5, a distillation column 6, an ion exchange resin column 7, a scrubber system 8, condensers 1a, 2a, 3a, 5a, and 6a, a heat exchanger 2b, and lines 11 to 46. The acetic acid production equipment X is configured so as to produce acetic acid continuously. The acetic acid production method according to the embodiment includes a reaction step, a flash evaporation step, a first distillation step, a second distillation step, a third distillation step, and an adsorption/removal step performed respectively in the reactor 1, the evaporator 2, the distillation column 3, the distillation column 5, the distillation column 6, and the ion exchange resin column 7, as described below.

The reactor 1 is a unit with which the reaction step is performed. The reaction step is the step of performing a reaction (methanol carbonylation reaction) represented by Reaction Formula (1) to form acetic acid continuously. A reaction mixture, which is continuously stirred typically with a stirrer, is present in the reactor 1 during steady operation of the acetic acid production equipment X. The reaction mixture includes starting materials methanol and carbon monoxide, a catalyst, a promoter, water, target acetic acid to be produced, and various by-products. In the reaction mixture, a liquid phase and a gas phase (vapor phase) are in equilibrium.

[Chem. 1]

$$CH_3OH+CO \rightarrow CH_3COOH \qquad (1)$$

The starting materials in the reaction mixture are liquid methanol and gaseous carbon monoxide. The methanol is fed from a methanol reservoir (not shown) through the line 11 to the reactor 1 continuously at a predetermined flow rate. The carbon monoxide is fed from a carbon monoxide reservoir (not shown) through the line 12 to the reactor 1 continuously at a predetermined flow rate.

The catalyst in the reaction mixture plays the role of promoting the methanol carbonylation reaction. The catalyst may be selected typically from rhodium catalysts and iridium catalysts. A non-limiting example of the rhodium catalysts is a rhodium complex represented by the chemical formula $[Rh(CO)_2I_2]^-$. A non-limiting example of the iridium catalysts is an iridium complex represented by the chemical formula $[Ir(CO)_2I_2]^-$. The reaction mixture may have a catalyst concentration of typically 200 to 5000 ppm of the entire liquid phase in the reaction mixture.

The promoter may be an iodide to assist the activity of the catalyst. Non-limiting examples of the iodide as the promoter include methyl iodide and an ionic iodide. The methyl iodide can offer the action of promoting the catalysis of the catalyst. The reaction mixture may have a methyl iodide concentration of typically 1 to 20 mass percent of the entire liquid phase in the reaction mixture. The ionic iodide is an iodide that forms an iodine ion in the reaction liquid. The ionic iodide can offer the actions of stabilizing the catalyst and of restraining side reactions. Non-limiting examples of the ionic iodide include lithium iodide, sodium iodide, and potassium iodide. The reaction mixture may have an ionic iodide concentration of typically 1 to 25 mass percent of the entire liquid phase in the reaction mixture.

Water in the reaction mixture is a component that is necessary for forming acetic acid according to the reaction mechanism of the methanol carbonylation reaction, and is necessary for dissolving water-soluble components in the reaction system. The reaction mixture may have a water concentration of typically 0.1 to 15 mass percent of the entire liquid phase in the reaction mixture. The water concentration in the reaction mixture is preferably 15 mass percent or less for saving energy necessary for water removal in the acetic acid purification process, so as to produce acetic acid with greater efficiency. To control the water concentration, water may be fed to the reactor 1 continuously at a predetermined flow rate.

The acetic acid in the reaction mixture includes acetic acid previously charged into the reactor 1 before operation of the acetic acid production equipment X; and acetic acid formed as a main product of the methanol carbonylation reaction. The acetic acid can act as a solvent in the reaction system. The reaction mixture may have an acetic acid concentration of typically 50 to 90 mass percent, and preferably 60 to 80 mass percent, of the entire liquid phase in the reaction mixture.

A non-limiting example of major by-products in the reaction mixture is methyl acetate. The methyl acetate may be formed by the reaction between acetic acid and methanol. The reaction mixture may have a methyl acetate concentration of typically 0.1 to 30 mass percent of the entire liquid phase in the reaction mixture. Non-limiting examples of the by-products in the reaction mixture also include hydrogen iodide. The hydrogen iodide is formed via the reaction mechanism of the methanol carbonylation reaction when the catalyst alone or in combination with the promoter as above is used. The reaction mixture may have a hydrogen iodide concentration of typically 0.01 to 2 mass percent of the entire liquid phase in the reaction mixture. The reaction mixture may also include acetic anhydride, which is a by-product. The reaction mixture may have an acetic anhydride concentration of typically 0 to 5000 ppm, more typically 0.01 to 3000 ppm, and furthermore typically 0.01 to 1000 ppm, of the entire liquid phase in the reaction mixture. Non-limiting examples of the by-products also include hydrogen, methane, carbon dioxide, acetaldehyde, propionic acid, and alkyl iodides such as hexyl iodide.

Reaction conditions in the reactor 1 housing the reaction mixture as above may be set typically as follows. The reaction temperature may be set typically at 150° C. to 250° C.; the reaction pressure as a total pressure may be set typically at 2.0 to 3.5 MPa (absolute pressure); and the carbon monoxide partial pressure may be set typically at 0.5 to 1.8 MPa (absolute pressure), and preferably at 0.8 to 1.5 MPa (absolute pressure).

In the reactor 1 during equipment operation, various gas-phase components tend to be evolved or formed continuously with continuous formation of acetic acid, to thereby increase the total volume of vapors. The vapors in the reactor 1 typically include carbon monoxide, hydrogen, methane, carbon dioxide, acetic acid, methyl acetate, methyl iodide, hydrogen iodide, acetaldehyde, dimethyl ether, and water. The vapors may be drawn out of the reactor 1 through the line 13. The inside pressure of the reactor 1 may be controlled by regulating the amount of the vapors to be drawn out. For example, the inside pressure of the reactor 1 may be held constant. The vapors drawn out of the reactor 1 are introduced into the condenser 1a.

The condenser 1a cools and partially condenses the vapors from the reactor 1 to separate the vapors into condensate components and gaseous components. The condensate components typically include acetic acid, methyl acetate, methyl iodide, acetaldehyde, dimethyl ether, and water and are introduced and recycled from the condenser 1a through the line 14 into the reactor 1. The gaseous components typically include carbon monoxide, hydrogen, methane, and carbon dioxide and are fed from the condenser 1a through the line 15 to the scrubber system 8. The gaseous components from the condenser 1a are separated in the scrubber system 8, from which useful components (such as carbon monoxide) are recovered. The separation and recovery in the embodiment is performed according to a wet process using an absorbing liquid (absorbent) to collect useful components from the gaseous components. The separation and recovery may also be performed using pressure swing adsorption. The separated, recovered useful components are recycled typically by introducing the same from the scrubber system 8 through a recycling line (not shown) into the reactor 1. The treatment in the scrubber system 8 and the subsequent recycling to the reactor 1 as mentioned above can be applied to after-mentioned gaseous components fed from other condensers to the scrubber system 8.

Acetic acid is continuously formed in the reactor 1 during equipment operation, as described above. The reaction mixture containing the acetic acid is continuously drawn out of the reactor 1 at a predetermined flow rate and fed through the line 16 into the subsequent (downstream) evaporator 2.

The evaporator 2 is a unit with which the flash evaporation step is performed. The flash evaporation step is the step of partially evaporating the reaction mixture to separate the mixture into vapors and residual liquid components, where the reaction mixture is continuously introduced into the evaporator 2. The evaporation may be performed by decompressing the reaction mixture with or without heating. In the flash evaporation step, the vapor temperature may be typically 100° C. to 260° C.; the residual liquid component temperature may be typically 80° C. to 200° C.; and the internal pressure of the evaporator may be typically 50 to 1000 kPa (absolute pressure). The ratio (weight ratio) of the vapors to the residual liquid components, which are separated from each other in the flash evaporation step, is typically from 10:90 to 50:50. The vapors formed in the step typically include acetic acid, acetic anhydride, methyl acetate, methyl iodide, water, hydrogen iodide, methanol, acetaldehyde, dimethyl ether, and propionic acid and are continuously drawn out of the evaporator 2 to the line 17. A part of the vapors drawn out of the evaporator 2 is continuously introduced into the condenser 2a, and another part (or the remainder) of the vapors is continuously introduced, as a crude acetic acid stream, into the subsequent distillation column 3. The crude acetic acid stream may have an acetic acid concentration of typically 50 to 85 mass percent, and preferably 55 to 75 mass percent. The residual liquid components formed or separated in the step include the catalyst and the promoter which have been contained in the reaction mixture; and acetic acid, acetic anhydride, methyl acetate, methyl iodide, water, and any other substances that remain without volatilization in the step. The residual liquid components are continuously introduced from the evaporator 2 through the line 18 into the heat exchanger 2b.

The condenser 2a cools and partially condenses the vapors from the evaporator 2 to separate the vapors into condensate components and gaseous components. The condensate components typically include acetic acid, methanol, methyl acetate, methyl iodide, acetaldehyde, dimethyl ether, and water and are introduced and recycled from the condenser 2a through the lines 19 and 20 into the reactor 1. The gaseous components typically include carbon monoxide and hydrogen and are fed from the condenser 2a through the lines 21 and 15 to the scrubber system 8. The acetic acid formation reaction in the reaction step is an exothermic reaction. In the flash evaporation step, a part of heat accumulated in the reaction mixture is transferred to the vapors derived from the reaction mixture. The condensate components formed by cooling of the vapors in the condenser 2a are recycled to the reactor 1. Namely, the acetic acid production equipment X is capable of efficiently removing heat generated in the methanol carbonylation reaction, by the working of the condenser 2a.

The heat exchanger 2b cools the residual liquid components from the evaporator 2. The cooled residual liquid components are continuously introduced and recycled from the heat exchanger 2b through the lines 22 and 20 into the reactor 1. Namely, the acetic acid production equipment X is capable of efficiently removing heat generated in the methanol carbonylation reaction, by the working of the heat exchanger 2b.

The distillation column 3 is a unit with which the first distillation step is performed. The distillation column 3 in the embodiment is positioned as a so-called low-boiling component removing column. The first distillation step is the step of subjecting the vapors to distillation to purify acetic acid in the vapors, where the vapors are continuously introduced into the distillation column 3. The distillation column 3 may include a column selected typically from rectification columns such as plate columns and packed columns. The distillation column 3, when being a plate column, may typically have 5 to 50 theoretical plates and may have a reflux ratio of typically 0.5 to 3000 according to the number of the theoretical plates. In the interior of the distillation column 3 during the first distillation step, the column top pressure may be set typically at 80 to 160 kPa (gauge pressure), and the bottom pressure may be set at a pressure which is higher than the column top pressure and which is typically from 85 to 180 kPa (gauge pressure). In the interior of the distillation column 3 during the first distillation step, the column top temperature may be set typically at a temperature which is lower than the boiling temperature of acetic acid at the set column top pressure and which is from 90° C. to 130° C.; and the bottom temperature may be set typically at a temperature which is approximately equal to or higher than the boiling point of acetic acid at the set bottom pressure and which is from 120° C. to 160° C.

Into the distillation column 3, the crude acetic acid stream (vapor) from the evaporator 2 is continuously introduced. At the distillation column 3, vapors are continuously drawn out as an overhead stream from the column top to the line 23; a bottom liquid is continuously drawn out from the column bottom to the line 24; and a first acetic acid stream (liquid) as a side stream is continuously drawn out of the distillation column 3 at a height level between the column top and the column bottom, to the line 25.

The vapors drawn out from the column top of the distillation column 3 are enriched with low-boiling components as compared with the bottom liquid from the distillation column 3, where the low-boiling components have lower boiling points as compared with acetic acid. The vapors typically include methyl acetate, methyl iodide, hydrogen iodide, acetaldehyde, methanol, dimethyl ether, and water. The vapors also include acetic acid. The vapors as above are continuously introduced through the line 23 into the condenser 3a.

The condenser 3a cools and partially condenses the vapors from the distillation column 3 to separate the vapors into condensate components and gaseous components. The condensate components typically include methyl acetate, methanol, methyl iodide, hydrogen iodide, acetaldehyde, dimethyl ether, water, and acetic acid and are continuously introduced from the condenser 3a through the line 26 into the decanter 4. The condensate components introduced into the decanter 4 are separated into an aqueous phase and an organic phase. The aqueous phase includes water typically with methyl acetate, methyl iodide, hydrogen iodide, acetaldehyde, dimethyl ether, methanol, and acetic acid. The organic phase typically includes methyl acetate, acetaldehyde, dimethyl ether, methyl iodide, hydrogen iodide, methanol, and acetic acid. In the embodiment, a part of the aqueous phase is refluxed (returned) through the line 27 into the distillation column 3, and another part (or the remainder) of the aqueous phase is introduced and recycled through the lines 27 and 20 into the reactor 1. A part of the organic phase is introduced and recycled through the lines 28 and 20 into the reactor 1, and another part (or the remainder) of the organic phase is introduced through the line 28 into an acetaldehyde removing unit (not shown). Since a part of the condensate components formed by cooling in the condenser 3a is recycled via the decanter 4 to the reactor 1, the acetic acid production equipment X enables efficient heat removal by the working of the condenser 3a. In contrast, the gaseous components formed in the condenser 3a typically include carbon monoxide, carbon dioxide, hydrogen, nitrogen, methane, acetic acid, methyl acetate, methanol, water, acetaldehyde, dimethyl ether, methyl iodide, and hydrogen iodide and are fed from the condenser 3a through the lines 29 and 15 to the scrubber system 8. Methyl iodide, hydrogen iodide, and other condensable gaseous components in the gaseous components coming into the scrubber system 8 are absorbed by an absorbing liquid (absorbent) in the scrubber system 8. In the scrubber system 8, the hydrogen iodide in the absorbing liquid reacts with methanol or methyl acetate to form methyl iodide. Such a liquid containing useful components such as the methyl iodide is introduced or recycled from the scrubber system 8 through the recycling line (not shown) into the reactor 1, to be reused.

The bottom liquid drawn out from the bottom of the distillation column 3 is enriched with high-boiling components as compared with the overhead stream from the distillation column 3, where the high-boiling components have higher boiling points as compared with acetic acid. The bottom liquid typically includes propionic acid, acetic anhydride, and the catalyst and the promoter as entrained. The bottom liquid also typically includes acetic acid, methyl iodide, methyl acetate, and water. In the embodiment, a part of the bottom liquid is continuously introduced and recycled through the line 24 into the evaporator 2, and another part (or the remainder) of the bottom liquid is continuously introduced and recycled through the lines 24 and 20 into the reactor 1.

The first acetic acid stream continuously drawn, as a side stream, out of the distillation column 3 is enriched with acetic acid as compared with the crude acetic acid stream continuously fed to the distillation column 3. Namely, the first acetic acid stream has a higher acetic acid concentration as compared with the crude acetic acid stream. The first acetic acid stream may have an acetic acid concentration of typically 90 to 99.9 mass percent, as long as being higher than the acetic acid concentration in the crude acetic acid stream. The first acetic acid stream further includes other components such as methyl acetate, methanol, methyl iodide, acetic anhydride, water, acetaldehyde, dimethyl ether, and hydrogen iodide, in addition to acetic acid. In the embodiment, the first acetic acid stream is drawn out of the distillation column 3 at a level lower than the level at which the crude acetic acid stream is introduced into the distillation column 3, where the levels are defined with respect to the height direction of the distillation column 3. The first acetic acid stream from the distillation column 3 is introduced through the line 25 into the subsequent distillation column 5 continuously at a predetermined flow rate.

The distillation column 5 is a unit with which the second distillation step is performed. The distillation column 5 in the embodiment is positioned as a so-called dehydration column. The second distillation step is the step of subjecting the first acetic acid stream to distillation to further purify the first acetic acid stream, where the first acetic acid stream is continuously introduced into the distillation column 5. The distillation column 5 may include a column selected typically from rectification columns such as plate columns and packed columns. The distillation column 5, when being a plate column, may typically have 5 to 50 theoretical plates and may have a reflux ratio of typically 0.5 to 3000 according to the number of the theoretical plates. In the interior of the distillation column 5 during the second distillation step, the column top pressure may be set typically at 150 to 250 kPa (gauge pressure), and the bottom pressure may be set at a pressure which is higher than the column top pressure and which is typically from 160 to 290 kPa (gauge pressure). In the interior of the distillation column 5 during the second distillation step, the column top temperature may be set typically at a temperature which is higher than the boiling point of water and lower than the boiling point of acetic acid each at the set column top pressure, and which is from 130° C. to 155° C.; and the bottom temperature may be set typically at a temperature which is equal to or higher than the boiling point of acetic acid at the set bottom pressure and which is from 150° C. to 180° C.

Into the distillation column 5, the first acetic acid stream (liquid) is continuously introduced from the distillation column 3. At the distillation column 5, vapors as an overhead stream are continuously drawn out from the column top to the line 30; and a bottom liquid is continuously drawn out from the column bottom to the line 31. Also at the distillation column 5, a side stream (liquid or gas) may be continuously drawn out to the line 32 at a height level between the column top and the column bottom.

The vapors drawn out from the top of the distillation column 5 are enriched with low-boiling components as compared with the bottom liquid from the distillation column 5, where the low-boiling components have lower boiling points as compared with acetic acid. Thus, the vapors typically include water, methyl acetate, methanol, methyl iodide, hydrogen iodide, dimethyl ether, and acetaldehyde. The vapors are continuously introduced through the line 30 into the condenser 5a.

The condenser 5a cools and partially condenses the vapors from the distillation column 5 to separate the vapors into condensate components and gaseous components. The condensate components typically include water, methyl acetate, methanol, methyl iodide, hydrogen iodide, dimethyl ether, and acetaldehyde. A part of the condensate components is continuously refluxed from the condenser 5a through the line 33 to the distillation column 5; and another part (or the remainder) of the condensate components is continuously introduced and recycled from the condenser 5a through the lines 33 and 34 into the reactor 1. This configuration allows the acetic acid production equipment X to efficiently remove heat at the condenser 5a. The gaseous components formed in the condenser 5a typically include water, methyl acetate, methanol, methyl iodide, hydrogen iodide, dimethyl ether, and acetaldehyde and are fed from the condenser 5a through the lines 35 and 15 to the scrubber system 8. Methyl iodide, hydrogen iodide, and other condensable gaseous components in the gaseous components coming into the scrubber system 8 are absorbed by the absorbing liquid in the scrubber system 8. In the absorbing liquid, the hydrogen iodide reacts with methanol or methyl acetate to form methyl iodide. Such a liquid containing useful components such as the methyl iodide is introduced or recycled from the scrubber system 8 through the recycling line (not shown) into the reactor 1, to be reused.

The bottom liquid drawn out from the bottom of the distillation column 5 is enriched with high-boiling components as compared with the overhead stream from the distillation column 5, where the high-boiling components have higher boiling points as compared with acetic acid. The bottom liquid typically includes propionic acid, acetic anhydride, and the catalyst and the promoter as entrained. The bottom liquid also includes acetic acid. The bottom liquid as above is fed through the line 31 to the line 32 to form a second acetic acid stream and is continuously introduced into the subsequent distillation column 6. Assume that the side stream is continuously drawn out of the distillation column 5 to the line 32. In this case, the side stream and the bottom liquid from the distillation column 5 are merged with each other to form the second acetic acid stream, and the resulting second acetic acid stream is continuously introduced into the subsequent distillation column 6.

The second acetic acid stream is enriched with acetic acid as compared with the first acetic acid stream continuously introduced into the distillation column 5. Namely, the second acetic acid stream has a higher acetic acid concentration as compared with the first acetic acid stream. The second acetic acid stream may have an acetic acid concentration of typically 99.1 to 99.99 mass percent, as long as being higher than the acetic acid concentration of the first acetic acid stream. The second acetic acid stream further includes other components such as methyl acetate, methyl iodide, water, acetic anhydride, and hydrogen iodide, in addition to acetic acid. In the embodiment, the side stream is drawn out of the distillation column 5 at a level lower than the level at which the first acetic acid stream is introduced into the distillation column 5, where the levels are defined with respect to the height direction of the distillation column 5.

In the acetic acid production equipment X, at least one substance selected from the group consisting of methanol, methyl acetate, and potassium hydroxide may be fed or added to the first acetic acid stream before being introduced through the line 25 into the distillation column 5, where the at least one substance is fed or added through the line 36, which is a supply line coupled to the line 25. This configuration is for restraining the concentration of corrosive iodines typically to 100 ppb or less in the first acetic acid stream introduced into the distillation column 5 and/or in the second acetic acid stream drawn out of the distillation column 5. The term "ppb" refers to "part by mass per billion" (ppb by mass). The substances to be added are prepared typically in the form of an aqueous solution. The amount of the at least one substance to be added may be determined typically on the basis of chemical composition analysis of a specimen sampled from the first acetic acid stream passing through the line 25. The corrosive iodines are such components that flow or pass, typically as accompanied with acetic acid, which is a main product in the reactor 1, through the units of the acetic acid production equipment X, and act as strong acids to cause corrosion of the acetic acid production equipment X. Decrease in such corrosive iodines is preferred for restraining the corrosion of the acetic acid production equipment X. As used herein, the term "corrosive iodines" refers to both iodine in the form of hydrogen iodide, and iodine (iodine ion) as dissociated from a counter ion. Also as used herein, the term "corrosive iodine concentration" refers to the total of concentrations of these corrosive iodines. The corrosive iodine concentration may be determined typically by coulometric titration of a liquid containing corrosive iodines (iodine in hydrogen iodide, and iodine ions) to be measured, where the titration is performed using a silver nitrate aqueous solution as a titrant. The coulometric titration may be performed typically with an automatic titrator (trade name COM-1600, supplied by HIRANUMA SANGYO CORPORATION). The hydrogen iodide concentration, which constitutes part of the corrosive iodine concentration, may be determined typically by determining an iodine ion concentration on the basis of the concentration of metal ions in the liquid and subtracting the iodine ion concentration from the corrosive iodine concentration. This is a technique for deriving the concentration on the assumption that the counter ion of metal ions in the liquid is an iodine ion. The metal ions in the liquid are trace amounts of metal ions derived from components in the material mixture, and trace amounts of free metal ions derived from (caused by) corrosion of constitutional members of the equipment. Non-limiting examples of the metal ions include Fe, Ni, Cr, Co, Mo, Mn, Al, Zn, and Zr. The metal ion concentration may be determined typically by inductively coupled plasma (ICP) emission spectrometry.

Feeding of methanol to the first acetic acid stream tends to decrease hydrogen iodide in the first acetic acid stream. Specifically, when methanol is fed, the hydrogen iodide concentration in the first acetic acid stream may be decreased so that two chemical reactions represented by Reaction Formula (2) reach equilibrium, where the two chemical reactions are a reaction between methanol and hydrogen iodide to form methyl iodide and water, and a reverse reaction thereof. Decrease of the hydrogen iodide concentration in the first acetic acid stream tends to also decrease the iodine ion concentration in the first acetic acid stream. Reaction Formula (2) is expressed as follows:

[Chem. 2]

$$CH_3OH + HI \rightleftharpoons CH_3I + H_2O \quad (2)$$

Feeding of methyl acetate to the first acetic acid stream tends to decrease hydrogen iodide in the first acetic acid stream. Specifically, when methyl acetate is fed, the hydrogen iodide concentration in the first acetic acid stream may be decreased so that two chemical reactions represented by Reaction Formula (3) reach equilibrium, where the two chemical reactions are a reaction between methyl acetate and hydrogen iodide to form methyl iodide and acetic acid, and a reverse reaction thereof. Reaction Formula (3) is expressed as follows:

[Chem. 3]

$$CH_3COOCH_3 + HI \rightleftharpoons CH_3I + CH_3COOH \quad (3)$$

Feeding of potassium hydroxide to the first acetic acid stream tends to decrease hydrogen iodide in the first acetic acid stream. Specifically, when potassium hydroxide is fed, the hydrogen iodide concentration in the first acetic acid stream may be decreased so that two chemical reactions represented by Reaction Formula (4) reach equilibrium, where the two chemical reactions are a reaction between potassium hydroxide and hydrogen iodide to form potassium iodide and water, and a reverse reaction thereof. The chemical equilibrium lies far to the right side in Reaction Formula (4). Reaction Formula (4) is expressed as follows:

[Chem. 4]

$$KOH + HI \rightleftharpoons KI + H_2O \quad (4)$$

The feeding or addition action to the first acetic acid stream before being introduced into the distillation column 5, as described above, contributes to a decreased abundance of hydrogen iodide in the distillation column 5 during distillation of the first acetic acid stream. This contributes to restrainment of thickening of hydrogen iodide and, in turn, to restrainment of thickening of corrosive iodine in the column top portion. The decreasing or lowering of the corrosive iodine concentration in the distillation column 5 is advantageous for restraining corrosion in the distillation column 5. Furthermore, the addition action is preferred for lowering the hydrogen iodide concentration in the first acetic acid stream from the distillation column 3, so as to control the corrosive iodine concentration in the second acetic acid stream from the distillation column 5 typically to 100 ppb or less. Lowering of the corrosive iodine concentration in the second acetic acid stream is advantageous for restraining corrosion in the units disposed downstream from the distillation column 5 in the acetic acid production equipment X.

The first acetic acid stream is introduced through the line 25 into the distillation column 5 in the acetic acid production equipment X and is subjected to the second distillation step. The first acetic acid stream in this stage includes acetic acid in a concentration of typically 90 mass percent or more, acetic anhydride, and water. Assume that the first acetic acid stream (acetic acid solution) passing through the line 25 is in such a state that the equilibrium concentration of acetic anhydride is higher than the acetic anhydride concentration. In this case, the first acetic acid stream may be subjected to a first acetic anhydride decreasing treatment in the distillation column 5. The first acetic anhydride decreasing treatment is the treatment of performing at least one of water concentration increasing and temperature lowering so as to bring the acetic acid solution into such a state that the equilibrium concentration of acetic anhydride is lower than the acetic anhydride concentration. As used herein, the term "equilibrium concentration of acetic anhydride" refers to an acetic anhydride concentration in an acetic acid solution when two chemical reactions (acetic anhydride hydrolysis reaction and a reverse reaction thereof) represented by Reaction Formula (5) in the acetic acid solution reaches equilibrium under the temperature condition and the pressure condition under which the acetic acid solution is present. The acetic anhydride hydrolysis reaction, namely, a reaction of acetic anhydride and water to form acetic acid, is an exothermic reaction. The reverse reaction, namely, a reaction of acetic acid to form acetic anhydride and water is an endothermic reaction. Reaction Formula (5) is expressed as follows:

[Chem. 5]

$$(CH_3CO)_2O + H_2O \rightleftharpoons 2CH_3COOH \quad (5)$$

In the first acetic anhydride decreasing treatment, the acetic acid solution having an acetic acid concentration of 90 mass percent or more and being in such a state that the equilibrium concentration of acetic anhydride is higher than the acetic anhydride concentration is subjected to water concentration increasing, or temperature lowering, or both in combination. The first acetic anhydride decreasing treatment, when performed, brings the high-concentration acetic acid solution in the distillation column 5 into such a state that the equilibrium concentration of acetic anhydride is lower than the acetic anhydride concentration. In the resulting acetic acid solution brought into this state, the acetic anhydride hydrolysis reaction proceeds so that the acetic anhydride concentration in the solution decreases toward or to the equilibrium concentration of acetic anhydride. In an embodiment as above, the acetic acid production method, which is performed with the acetic acid production equipment X, includes the first acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the first acetic acid stream (acetic acid solution) passing through the line 25 is in such a state that the equilibrium concentration of acetic anhydride is lower than the acetic anhydride concentration. In this case, the first acetic acid stream may be subjected to a second acetic anhydride decreasing treatment in the distillation column 5. The second acetic anhydride decreasing treatment is the treatment of performing at least one of water concentration increasing and temperature lowering so as to further lower the equilibrium concentration of acetic anhydride. In the second acetic anhydride decreasing treatment, the acetic acid solution having an acetic acid concentration of 90 mass percent or more and being in such a state that the equilibrium concentration of acetic anhydride is lower than the acetic anhydride concentration is subjected to water concentration increasing, or temperature lowering, or both in combination. The second acetic anhydride decreasing treatment, when performed, brings the high-concentration acetic acid solution in the distillation column 5 into such a state that the equilibrium concentration of acetic anhydride is further lowered. In the resulting acetic acid solution brought into this state, the acetic anhydride hydrolysis reaction tends to proceed so that the acetic anhydride concentration in the solution decreases toward or to the equilibrium concentration of acetic anhydride. In an embodiment as above, the acetic acid production method, which is performed with the acetic acid production equipment X, includes the second acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the first acetic acid stream (acetic acid solution) passing through the line 25 is in such a state that the equilibrium concentration of acetic anhydride is lower than the acetic anhydride concentration. In this case, the first acetic acid stream may be subjected to a third acetic anhydride decreasing treatment in the distillation column 5. The third acetic anhydride decreasing treatment is the treatment of performing temperature rising alone or in combination with water concentration increasing, as long as the state is maintained, so as to increase the reaction rate of acetic anhydride hydrolysis. In the third acetic anhydride decreasing treatment, the acetic acid solution having an acetic acid concentration of 90 mass percent or more and being in such a state that the equilibrium concentration of acetic anhydride is lower than the acetic anhydride concentration is subjected to temperature rising alone or in combination with water concentration increasing, while the state is maintained. The temperature rising alone or in combination with water concentration increasing, when performed on the acetic acid solution, kinetically advantageously acts on increase in reaction rate of acetic anhydride hydrolysis. The third acetic anhydride decreasing treatment, when performed on the high-concentration acetic acid solution in the distillation column 5, increases the reaction rate of acetic anhydride hydrolysis, with maintaining the state that the equilibrium concentration of acetic anhydride is lower than the acetic anhydride concentration. This promotes the acetic anhydride hydrolysis reaction so that the acetic anhydride concentration in the solution decreases toward or to the equilibrium concentration of acetic anhydride. In an embodiment as above, the acetic acid production method, which is performed with the acetic acid production equipment X, includes the third acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

The water concentration increasing in the above-mentioned first, second, and third acetic anhydride decreasing treatments may be performed by adding at least one of water and methanol to the first acetic acid stream introduced into the distillation column 5, where the at least one of water and methanol is added through the line 37, which is a supply line coupled to the distillation column 5. Feeding or addition of methanol may bring acetic acid to react with methanol to form methyl acetate and water, and this may lead to increase in water concentration. The addition of methanol to the acetic acid stream acts as a way to decrease hydrogen iodide, as described above relating to Reaction Formula (2), acts as a way to increase the water concentration and, consequently, acts as a way to decrease the acetic anhydride concentration. In the embodiment, at least one of water and methanol is added at a level (level at which the line 37 is coupled to the distillation column 5) lower than the level (level at which the line 25 is coupled to the distillation column 5) at which the first acetic acid stream is introduced, where the levels are defined with respect to the height direction of the distillation column 5. The first acetic acid stream being distilled in the distillation column 5, which acts as a dehydration column, has a decreasing water concentration with a lowering height level in the distillation column 5. Accordingly, the configuration that the level at which at least one of water and methanol is added is lower than the level at which the first acetic acid stream is introduced is advantageous for water concentration increasing, and consequently, advantageous for efficiency of the acetic anhydride decreasing treatment by the addition of at least one of water and methanol to the first acetic acid stream. The amount of the at least one of water and methanol to be added may be determined typically on the basis of chemical composition analysis of a specimen sampled from the first acetic acid stream passing through the line 25. The water concentration increasing of the first acetic acid stream in the distillation column 5 may also be performed by weakening heating and vaporizing at the bottom of the distillation column 5. The heating and vaporizing in the distillation column may be performed typically using a reboiler for heating the solution to be distilled. With weakening heating and vaporizing at the bottom of the distillation column 5, the reflux rate or reflux ratio in the distillation column 5 decreases to lower the separation efficiency, i.e., water separation capability of the distillation column 5, which serves as a dehydration column. This tends to result in increased water concentration of an acetic acid solution, such as a bottom liquid, present in a lower portion in the column. The first acetic acid stream (acetic acid solution), when in the state brought by any of the first, second, and third acetic anhydride decreasing treatments, may have a water concentration of typically 7 to 2500 ppm. The acetic acid solution is preferably controlled to have a water concentration of 2500 ppm or less. This is preferred for saving energy necessary for water removal in the acetic acid purification process, so as to produce acetic acid with greater efficiency.

The temperature lowering of the first acetic acid stream in the first and second acetic anhydride decreasing treatments may be performed by lowering the internal temperature of the distillation column 5. For example, the temperature of the first acetic acid stream in the distillation column 5 may be lowered by lowering the bottom temperature of the distillation column 5. The temperature rising of the first acetic acid stream in the third acetic anhydride decreasing treatment may be performed by raising the internal temperature of the distillation column 5. For example, the temperature of the first acetic acid stream in the distillation column 5 may be raised by raising the bottom temperature of the distillation column 5. The first acetic acid stream (acetic acid solution), when in the state brought by any of the first, second, and third acetic anhydride decreasing treatments, has a temperature which is equal to or higher than the melting point of acetic acid and is typically from 17° C. to 180° C. The internal temperature of the distillation column 5 may be controlled typically by adjusting the column internal pressure and/or adjusting the power of heating and vaporizing at the column bottom.

The first acetic acid stream (acetic acid solution), when in the state brought by any of the first, second, and third acetic anhydride decreasing treatments, is preferably controlled to have a water concentration of 2000 ppm or more and a temperature of 180° C. or lower, or to have a water concentration of 1000 ppm or more and a temperature of 170° C. or lower, or to have a water concentration of 500 ppm or more and a temperature of 120° C. or lower, or to have a water concentration of 200 ppm or more and a temperature of 100° C. or lower, or to have a water concentration of 80 ppm or more and a temperature of 60° C. or lower, or to have a water concentration of 40 ppm or more and a temperature of 50° C. or lower, or to have a water concentration of 12 ppm or more and a temperature of 30° C. or lower. These conditions may be determined according to the acetic anhydride concentration, which is typically 1 to 300 ppm, in the acetic acid solution. The residence time of the first acetic acid stream (acetic acid solution) after undergoing any of the first, second, and third acetic anhydride decreasing treatments is typically 1 second or longer, preferably 30 seconds or longer, more preferably 1 minute or longer, more preferably 5 minutes or longer, more preferably 10 minutes or longer, more preferably 30 minutes or longer, more preferably 60 minutes or longer, more preferably 900 minutes or longer, more preferably 1300 minutes or longer, more preferably 1400 minutes or longer, and more preferably 2800 minutes or longer. As used herein, the term "residence time" of the first acetic acid stream (acetic acid solution) after the acetic anhydride decreasing treatment refers to a time determined typically by dividing the total amount (typically in "$m^3$") of liquids, which change places, but remain in the distillation column 5 during operation, by the net flow rate (typically in "$m^3/h$") of acetic acid passing through the distillation column 5. These configurations on the water concentration, temperature, and residence time in the acetic anhydride decreasing treatments to be performed on the first acetic acid stream are advantageous for allowing the acetic anhydride hydrolysis reaction to proceed and for thereby decreasing the acetic anhydride concentration in the first acetic acid stream (acetic acid solution) in the distillation column 5.

The first, second, and third acetic anhydride decreasing treatments preferably allow a catalyst for promoting acetic anhydride hydrolysis to be present in the first acetic acid stream (acetic acid solution). For example, the first, second, and third acetic anhydride decreasing treatments may allow at least one substance selected typically from Broensted acids, Lewis acids, and corrodible metals to be present in the first acetic acid stream, where these substances are capable of functionally promoting acetic anhydride hydrolysis. In the embodiment, a solution containing the catalyst to be used may be added through the line 37, which is a supply line, to the first acetic acid stream in the distillation column 5. When a catalyst capable of functionally promoting acetic anhydride hydrolysis is generated/accumulated in the distillation column 5, the catalyst can be used in the embodiment. Non-limiting examples of such corrodible metals as to be generated/accumulated in distillation columns such as the distillation column 5 in the acetic acid production equipment X include Fe, Ni, Cr, Mo, Mn, Li, Co, Zr, Zn, and Al. The catalyst in the acetic acid solution may be present in an amount of preferably 0.01 to 10000 ppm. For offering sufficient catalysis, the catalyst in the acetic acid solution is present in an amount of preferably 0.1 ppm or more, more preferably 1 ppm or more, and furthermore preferably 10 ppm or more. When the catalyst is used in the first, second, and third acetic anhydride decreasing treatments, the acetic acid solution may have a temperature of typically 180° C. or lower, preferably 170° C. or lower, more preferably 160° C. or lower, more preferably 140° C. or lower, more preferably 120° C. or lower, and more preferably 40° C. or lower. When the catalyst is used in the first, second, and third acetic anhydride decreasing treatments, the residence time of the acetic acid solution is typically 1 second or longer, preferably 10 seconds or longer, more preferably 30 seconds or longer, and more preferably 1 minute or longer.

When the catalyst is used in the first, second, and third acetic anhydride decreasing treatments, the catalyst can offer its catalytic function in an acetic acid stream until it is removed in the course of the acetic acid purification process by the working of the acetic acid production equipment X.

The second acetic acid stream passing through the lines 31 and 32 between the distillation column 5 and the distillation column 6 in the acetic acid production equipment X typically includes acetic acid in a concentration of 90 mass percent or more, acetic anhydride, and water. Assume that the second acetic acid stream (acetic acid solution) passing through the lines 31 and 32 is in such a state that the equilibrium concentration of acetic anhydride is higher than the acetic anhydride concentration. In this case, the second acetic acid stream may be subjected to a first acetic anhydride decreasing treatment in the lines 31 and 32. The first acetic anhydride decreasing treatment is the treatment of performing at least one of water concentration increasing and temperature lowering so as to bring the acetic acid solution into such a state that the equilibrium concentration of acetic anhydride is lower than the acetic anhydride concentration. In the first acetic anhydride decreasing treatment, the acetic acid solution having an acetic acid concentration of 90 mass percent or more and being in such a state that the equilibrium concentration of acetic anhydride is higher than the acetic anhydride concentration is subjected to water concentration increasing, or temperature lowering, or both in combination. The first acetic anhydride decreasing treatment, when performed, brings the acetic acid solution in the lines 31 and 32 into such a state that the equilibrium concentration of acetic anhydride is lower than the acetic anhydride concentration. In the resulting acetic acid solution brought into this state, the acetic anhydride hydrolysis reaction proceeds so that the acetic anhydride concentration in the solution decreases toward or to the equilibrium concentration of acetic anhydride. In an embodiment as above, the acetic acid production method, which is performed with the acetic acid production equipment X, includes the first acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the second acetic acid stream (acetic acid solution) passing through the lines 31 and 32 is in such a state that the equilibrium concentration of acetic anhydride is lower than the acetic anhydride concentration. In this case, the second acetic acid stream may be subjected to a second acetic anhydride decreasing treatment in the lines 31 and 32. The second acetic anhydride decreasing treatment is the treatment of performing at least one of water concentration increasing and temperature lowering on the acetic acid solution so as to further lower the equilibrium concentration of acetic anhydride. In the second acetic anhydride decreasing treatment, the acetic acid solution having an acetic acid concentration of 90 mass percent or more and being in such a state that the equilibrium concentration of acetic anhydride is lower than the acetic anhydride concentration is subjected to water concentration increasing, or temperature lowering, or both in combination. The second acetic anhydride decreasing treatment, when performed on the high-concentration acetic acid solution in the lines 31 and 32, allows the equilibrium concentration of acetic anhydride to be further lowered. In the resulting acetic acid solution brought into this state, the acetic anhydride hydrolysis reaction tends to proceed so that the acetic anhydride concentration in the solution decreases toward or to the equilibrium concentration of acetic anhydride. In an embodiment as above, the acetic acid production method, which is performed with the acetic acid production equipment X, includes the second acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the second acetic acid stream (acetic acid solution) passing through the lines 31 and 32 is in such a state that the equilibrium concentration of acetic anhydride is lower than the acetic anhydride concentration. In this case, the second acetic acid stream in the lines 31 and 32 may be subjected to a third acetic anhydride decreasing treatment. The third acetic anhydride decreasing treatment is the treatment of performing temperature rising alone or in combination with water concentration increasing so as to increase the reaction rate of acetic anhydride hydrolysis, as long as the state is maintained. In an acetic acid solution in such a state that the equilibrium concentration of acetic anhydride is lower than the acetic anhydride concentration, the acetic anhydride concentration has a tendency to decrease as the state is maintained. So as to promote or enhance this tendency by increasing the reaction rate of acetic anhydride hydrolysis, the third acetic anhydride decreasing treatment subjects the acetic acid solution having an acetic acid concentration of 90 mass percent or more and being in such a state that the equilibrium concentration of acetic anhydride is lower than the acetic anhydride concentration to temperature rising alone or in combination with water concentration increasing, while the state is maintained. The temperature rising alone or in combination with water concentration increasing of the acetic acid solution acts kinetically advantageously on the reaction rate increase of acetic anhydride hydrolysis. The third acetic anhydride decreasing treatment, when performed on the high-concentration acetic acid solution passing through the lines 31 and 32, increases the reaction rate of acetic anhydride hydrolysis while maintaining the equilibrium concentration of acetic anhydride being lower than the acetic anhydride concentration. This promotes the acetic anhydride hydrolysis reaction so that the acetic anhydride concentration in the solution decreases toward or to the equilibrium concentration of acetic anhydride. In an embodiment as above, the acetic acid production method, which is performed with the acetic acid production equipment X, includes the third acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

The water concentration increasing of the second acetic acid stream in any of the first, second, and third acetic anhydride decreasing treatments may be performed by adding water through the line 38, which is a supply line coupled to the line 31. The amount of water to be added may be determined typically on the basis of chemical composition analysis of a specimen sampled from the second acetic acid stream passing through the lines 31 and 32. The second acetic acid stream (acetic acid solution), when in the state brought by any of the first, second, and third acetic anhydride decreasing treatments, may have a water concentration of typically 7 to 2500 ppm. The acetic acid solution is preferably controlled to have a water concentration of 2500 ppm or less. This is preferred for saving energy necessary for water removal in the acetic acid purification process, so as to produce acetic acid with greater efficiency.

The temperature lowering of the second acetic acid stream in the first and second acetic anhydride decreasing treatments may be performed using a cooler (not shown) or a condenser (not shown) each disposed at the lines 31 and 32. The cooler may typically be a heat exchanger which is configured for cooling use (this is also applicable to after-mentioned coolers). The temperature rising of the second acetic acid stream in the third acetic anhydride decreasing treatment may be performed using a heater (not shown) disposed at the lines 31 and 32. The heater may typically be a heat exchanger which is configured for heating use (this is also applicable to after-mentioned heaters). The second acetic acid stream (acetic acid solution), when in the state brought by any of the first, second, and third acetic anhydride decreasing treatments, may have a temperature which is equal to or higher than the melting point of acetic acid and which is typically from 17° C. to 180° C.

The second acetic acid stream (acetic acid solution), when in the state brought by any of the first, second, and third acetic anhydride decreasing treatments, is preferably controlled to have a water concentration of 2000 ppm or more and a temperature of 180° C. or lower, or to have a water concentration of 1000 ppm or more and a temperature of 170° C. or lower, or to have a water concentration of 500 ppm or more and a temperature of 120° C. or lower, or to have a water concentration of 200 ppm or more and a temperature of 100° C. or lower, or to have a water concentration of 80 ppm or more and a temperature of 60° C. or lower, or to have a water concentration of 40 ppm or more and a temperature of 50° C. or lower, or to have a water concentration of 12 ppm or more and a temperature of 30° C. or lower. These conditions may be determined according to the acetic anhydride concentration, which is typically 1 to 300 ppm, in the acetic acid solution. The residence time of the second acetic acid stream (acetic acid solution) after undergoing any of the first, second, and third acetic anhydride decreasing treatments, is typically 1 second or longer, preferably 30 seconds or longer, more preferably 1 minute or longer, more preferably 5 minutes or longer, more preferably 10 minutes or longer, more preferably 30 minutes or longer, more preferably 60 minutes or longer, more preferably 900 minutes or longer, more preferably 1300 minutes or longer, more preferably 1400 minutes or longer, and more preferably 2800 minutes or longer. As used herein, the term "residence time" of the second acetic acid stream (acetic acid solution) after any of the acetic anhydride decreasing treatments refers to a time necessary for the acetic acid solution to reach the distillation column 6 from a point at which the treatment is performed in the lines 31 and 32 (e.g., the point at which the line 38 is coupled). A relatively long residence time may be achieved typically by disposing a buffer tank in the midway of the line 32. When a buffer tank is disposed in the midway of the second acetic acid stream zone in the line 32, the "residence time" of the second acetic acid stream after the acetic anhydride decreasing treatment also includes the time during which the acetic acid solution remains in the tank. The above-mentioned configurations on the water concentration, temperature, and residence time of the second acetic acid stream in the acetic anhydride decreasing treatments are advantageous for allowing the acetic anhydride hydrolysis reaction to proceed and for thereby decreasing the acetic anhydride concentration in the second acetic acid stream (acetic acid solution).

The first, second, and third acetic anhydride decreasing treatments performed on the second acetic acid stream, preferably allow a catalyst for promoting acetic anhydride hydrolysis to be present in the second acetic acid stream (acetic acid solution). For example, the first, second, and third acetic anhydride decreasing treatments, when performed on the second acetic acid stream, may allow at least one substance selected from Broensted acids, Lewis acids, and corrodible metals to be present in the second acetic acid stream, where these substances are capable of functionally promoting acetic anhydride hydrolysis. In the embodiment, a solution containing a catalyst to be used may be added through the line 38, which is a supply line, to the second acetic acid stream in the lines 31 and 32. The catalyst in the acetic acid solution may be present in an amount of preferably 0.01 to 10000 ppm. From the viewpoint of offering sufficient catalysis, the catalyst in the acetic acid solution may be present in an amount of preferably 0.1 ppm or more, more preferably 1 ppm or more, and furthermore preferably 10 ppm or more. When the first, second, and third acetic anhydride decreasing treatments performed on the second acetic acid stream employ a catalyst, the acetic acid solution may have a temperature of typically 180° C. or lower, preferably 170° C. or lower, more preferably 160° C. or lower, more preferably 140° C. or lower, more preferably 120° C. or lower, and more preferably 40° C. or lower. When the first, second, and third acetic anhydride decreasing treatments performed on the second acetic acid stream employ a catalyst, the residence time of the acetic acid solution may be typically 1 second or longer, preferably 10 seconds or longer, more preferably 30 seconds or longer, and furthermore preferably 1 minute or longer. When the first, second, and third acetic anhydride decreasing treatments performed on the second acetic acid stream employ a catalyst, the catalyst can offer its catalytic function in an acetic acid stream until it is removed in the course of acetic acid purification process by the working of the acetic acid production equipment X.

The distillation column 6 is a unit with which the third distillation step is performed and is positioned as a so-called high-boiling component removing distillation column in the embodiment. The third distillation step is the step of distilling the second acetic acid stream continuously introduced into the distillation column 6, so as to further purify acetic acid. The distillation column 6 may include a column selected from rectification columns such as plate columns and packed columns. The distillation column 6, when being a plate column, may typically have 5 to 50 theoretical plates and may have a reflux ratio of typically 0.5 to 3000, according to the number of the theoretical plates. In the interior of the distillation column 6 during the third distillation step, the column top pressure may be set typically at −100 to 150 kPa (gauge pressure), and the column bottom pressure may be set at a pressure which is higher than the column top pressure and which is from −90 to 180 kPa (gauge pressure). In the interior of the distillation column 6 during the third distillation step, the column top temperature may be set at a temperature which is higher than the boiling temperature of water, but lower than the boiling temperature of acetic acid each at the set column top pressure and which is from 50° C. to 150° C.; and the column bottom temperature may be set typically at a temperature which is higher than the boiling point of acetic acid at the set column bottom pressure and which is from 70° C. to 180° C.

Into the distillation column 6, the second acetic acid stream (liquid) is continuously introduced through the line 32. At the distillation column 6, vapors as an overhead stream are continuously drawn out from the column top to the line 39; a bottom liquid is continuously drawn out from the column bottom to the line 40; and a side stream (liquid or gas) is continuously drawn out to the line 41 at a height level between the column top and the column bottom in the distillation column 6. When a gas is drawn out as a side stream from the distillation column 6, the side stream is converted into a liquid typically by passing through a condenser or cooler in the course of passing through the line 41. In an embodiment, the line 41 is coupled to the distillation column 6 at a level higher than the level at which the line 32 is coupled, as illustrated in the FIGURE, where the levels are defined in terms of the height direction of the distillation column 6. Instead of this configuration, the line 41 may be coupled to the distillation column 6 at a level lower than, or at a level equal to, the level at which the line 32 is coupled to the distillation column 6.

The vapors drawn out from the column top of the distillation column 6 are enriched with low-boiling components as compared with the bottom liquid from the distillation column 6, where the low-boiling components have lower boiling points as compared with acetic acid. The vapors typically include hydrogen iodide, methyl acetate, methyl iodide, water, acetaldehyde, formic acid, and crotonaldehyde. The vapors also include acetic acid. These vapors are continuously introduced through the line 39 into the condenser 6a.

The condenser 6a cools and partially condenses the vapors from the distillation column 6 to separate the vapors into condensate components and gaseous components. The condensate components typically include acetic acid and hydrogen iodide. At least a part of the condensate components is continuously refluxed from the condenser 6a through the line 42 to the distillation column 6. Another part (distillate) of the condensate components can be recycled from the condenser 6a through the lines 42 and 43 to the first acetic acid stream in the line 25, which first acetic acid solution is before being introduced into the distillation column 5. A part of the distillate from the condenser 6a may be fed to the scrubber system 8 and be used as an absorbing liquid in the system. At the scrubber system 8, hydrogen iodide and other gaseous components are separated from the distillate and are discharged out of the equipment; and a liquid containing useful components is introduced or recycled from the scrubber system 8 through the recycling line (not shown) into the reactor 1, to be reused. The useful components include acetic acid and methyl iodide. The methyl iodide includes methyl iodide formed by a reaction of hydrogen iodide with methanol or methyl acetate in the absorbing liquid. In addition, a part of the distillate from the condenser 6a may be introduced through a line (not shown) into various pumps (not shown) operated in the equipment and be used as a sealant (sealing liquid) for the pumps. Further, a part of the distillate from the condenser 6a may be drawn out of the equipment steadily, or non-steadily as needed. The drawing is performed through a drawing line attached to the line 42. In contrast, the gaseous components separated in the condenser 6a typically include carbon monoxide, hydrogen, carbon dioxide, methane, nitrogen, and hydrogen iodide and are fed from the condenser 6a through the lines 44 and 15 to the scrubber system 8.

The bottom liquid drawn out from the bottom of the distillation column 6 through the line 40 is enriched with high-boiling components as compared with the overhead stream from the distillation column 6, where the high-boiling components have higher boiling points as compared with acetic acid. The bottom liquid typically includes propionic acid. The bottom liquid drawn out from the bottom of the distillation column 6 through the line 40 also include corrodible metals which are formed in, and liberated from, the inner walls of members or components constituting the acetic acid production equipment X; and compounds between the corrodible metals and iodines derived from corrosive iodines. The bottom liquid as above is discharged from the acetic acid production equipment X in the embodiment. Instead of this, it is also acceptable that a part of the bottom liquid is discharged from the equipment and another part (or the remainder) of the bottom liquid is recycled to the line 25.

The side stream continuously drawn out of the distillation column 6 to the line 41 is continuously introduced, as a third acetic acid stream, into the subsequent ion exchange resin column 7. The third acetic acid stream is enriched with acetic acid as compared with the second acetic acid stream continuously introduced into the distillation column 6. Specifically, the third acetic acid stream has a higher acetic acid concentration as compared with the second acetic acid stream. The third acetic acid stream may have an acetic acid concentration of typically 99.8 to 99.999 mass percent, as long as being higher than the acetic acid concentration of the second acetic acid stream. In the embodiment, the side stream is drawn out of the distillation column 6 at a level higher than the level at which the second acetic acid stream is introduced into the distillation column 6, where the levels are defined in terms of the height direction of the distillation column 6. In another embodiment, the side stream is drawn out of the distillation column 6 at a level lower than the level at which the second acetic acid stream is introduced into the distillation column 6, where the levels are defined in terms of the height direction of the distillation column 6.

In the acetic acid production equipment X, a part of the overhead (overhead distillate) from the distillation column 6 may be recycled through the lines 42 and 43 to the first acetic acid stream before being introduced into the distillation column 5, so as to decrease the corrosive iodine concentration in the second acetic acid stream in the distillation column 6. In this configuration, of the overhead from the distillation column 6, corrosive iodines contained in the liquid stream to be recycled to the first acetic acid stream will again undergo the second distillation step in the distillation column 5 and the third distillation step in the distillation column 6.

Specifically, corrosive iodines contained in the liquid stream to be recycled to the first acetic acid stream will again undergo a purification path centered on the distillation column 5 and a purification path centered on the distillation column 6. In the embodiment, the purification path centered on the distillation column 5 includes a channel to perform a reaction of hydrogen iodide with methanol or methyl acetate to form methyl iodide in the scrubber system 8 and for thereby decreasing hydrogen iodide; and a channel to discharge iodine-containing chemical species through the scrubber system 8 out of the equipment, where the chemical species are derived from corrosive iodines. In the embodiment, the purification path centered on the distillation column 6 includes a channel to perform a reaction of hydrogen iodide with methanol or methyl acetate to form methyl iodide to decrease hydrogen iodide in the scrubber system 8; and a channel to discharge compounds between corrodible metals and iodines from the distillation column 6 through the line 40 out of the equipment, where the iodines are derived from corrosive iodines. Assume that the liquid stream to be recycled from the distillation column 5 to the reactor 1 includes corrosive iodines. In this case, the corrosive iodines have the opportunity of again undergoing the purification paths centered on the distillation columns 5 and 6, where the channels include a channel in which the corrosive iodines can be converted into methyl iodide. The configuration as above is advantageous for decreasing the abundances of hydrogen iodide and iodine ions and for thereby decreasing the corrosive iodine concentration in the acetic acid stream (second acetic acid stream) in the distillation column 6, which is disposed downstream from the distillation column 5 in the purification system.

The third acetic acid stream passing through the line 41 from the distillation column 6 to the ion exchange resin column 7 in the acetic acid production equipment X typically includes acetic acid in a concentration of 90 mass percent or more, acetic anhydride, and water. Assume that the third acetic acid stream (acetic acid solution) passing through the line 41 is in such a state that the equilibrium concentration of acetic anhydride is higher than the acetic anhydride concentration. In this case, the third acetic acid stream may be subjected to a first acetic anhydride decreasing treatment in the line 41. The first acetic anhydride decreasing treatment is the treatment of performing at least one of water concentration increasing and temperature lowering so as to bring the acetic acid solution into such a state that the equilibrium concentration of acetic anhydride is lower than the acetic anhydride concentration. In the first acetic anhydride decreasing treatment, the acetic acid solution having an acetic acid concentration of 90 mass percent or more and being in such a state that the equilibrium concentration of acetic anhydride is higher than the acetic anhydride concentration is subjected to water concentration increasing, or temperature lowering, or both in combination. The first acetic anhydride decreasing treatment as above, when performed on the high-concentration acetic acid solution in the line 41, brings the acetic acid solution into such a state that the equilibrium concentration of acetic anhydride is lower than the acetic anhydride concentration. In the resulting acetic acid solution brought into this state, the acetic anhydride hydrolysis reaction proceeds so that the acetic anhydride concentration in the solution decreases toward or to the equilibrium concentration of acetic anhydride. In an embodiment as above, the acetic acid production method, which is performed with the acetic acid production equipment X, includes the first acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the third acetic acid stream (acetic acid solution) passing through the line 41 is in such a state that the equilibrium concentration of acetic anhydride is lower than the acetic anhydride concentration. In this case, the third acetic acid stream may be subjected to a second acetic anhydride decreasing treatment in the line 41. The second acetic anhydride decreasing treatment is the treatment of performing at least one of water concentration increasing and temperature lowering so as to further lower the equilibrium concentration of acetic anhydride. In the second acetic anhydride decreasing treatment herein, the acetic acid solution having an acetic acid concentration of 90 mass percent or more and being in such a state that the equilibrium concentration of acetic anhydride is lower than the acetic anhydride concentration is subjected to water concentration increasing, or temperature lowering, or both in combination. The second acetic anhydride decreasing treatment as above, when performed on the high-concentration acetic acid solution in the line 41, allows the equilibrium concentration of acetic anhydride to be further lowered. In the resulting acetic acid solution brought into this state, the acetic anhydride hydrolysis reaction tends to proceed so that the acetic anhydride concentration in the solution decreases toward or to the equilibrium concentration of acetic anhydride. In an embodiment as above, the acetic acid production method, which is performed with the acetic acid production equipment X, includes the second acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the third acetic acid stream (acetic acid solution) passing through the line 41 is in such a state that the equilibrium concentration of acetic anhydride is lower than the acetic anhydride concentration. In this case, the third acetic acid stream may be subjected to a third acetic anhydride decreasing treatment in the line 41. The third acetic anhydride decreasing treatment is the treatment of performing temperature rising alone or in combination with water concentration increasing, as long as the state is maintained, so as to increase the reaction rate of acetic anhydride hydrolysis. In an acetic acid solution being in such a state that the equilibrium concentration of acetic anhydride is lower than the acetic anhydride concentration, the acetic anhydride concentration has a tendency to decrease, as long as the state is maintained. So as to promote or enhance this tendency by increasing the reaction rate of acetic anhydride hydrolysis, the third acetic anhydride decreasing treatment subjects the acetic acid solution having an acetic acid concentration of 90 mass percent or more and being in such a state that the equilibrium concentration of acetic anhydride is lower than the acetic anhydride concentration to temperature rising alone or in combination with water concentration increasing, while the state is maintained. The temperature rising alone or in combination with water concentration increasing of the acetic acid solution kinetically advantageously acts on increase of the reaction rate of acetic anhydride hydrolysis. The third acetic anhydride decreasing treatment, when performed on the high-concentration acetic acid solution passing through the line 41, increases the reaction rate of acetic anhydride hydrolysis while maintaining the equilibrium concentration of acetic anhydride being lower than the acetic anhydride concentration. This promotes the acetic anhydride hydrolysis reaction so that the acetic anhydride concentration in the solution decreases toward or to the equilibrium concentration of acetic anhydride. In an embodiment as above, the acetic acid production method, which is performed with the acetic acid production equipment X, includes the third acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

The water concentration increasing of the third acetic acid stream in the first, second, and third acetic anhydride decreasing treatments may be performed by adding water through the line 45, which is a supply line coupled to the line 41. The amount of water to be added may be determined typically on the basis of chemical composition analysis of a specimen sampled from the third acetic acid stream passing through the line 41. The third acetic acid stream (acetic acid solution), when in the state brought by any of the first, second, and third acetic anhydride decreasing treatments, may have a water concentration of typically 7 to 2500 ppm. The acetic acid solution is preferably controlled to have a water concentration of 2500 ppm or less. This is preferred for saving energy necessary for water removal in the acetic acid purification process, so as to produce acetic acid with greater efficiency.

The temperature lowering of the third acetic acid stream in the first and second acetic anhydride decreasing treatments may be performed using a cooler (not shown) or a condenser (not shown) each disposed at the line 41. The temperature rising of the third acetic acid stream in the third acetic anhydride decreasing treatment may be performed using a heater (not shown) disposed at the line 41. The third acetic acid stream (acetic acid solution), when in the state brought by any of the first, second, and third acetic anhydride decreasing treatments, may have a temperature which is equal to or higher than the melting point of acetic acid and which is typically from 17° C. to 180° C.

The third acetic acid stream (acetic acid solution), when in the state brought by any of the first, second, and third acetic anhydride decreasing treatments, is preferably controlled to have a water concentration of 2000 ppm or more and a temperature of 180° C. or lower, or to have a water concentration of 1000 ppm or more and a temperature of 170° C. or lower, or to have a water concentration of 500 ppm or more and a temperature of 120° C. or lower, or to have a water concentration of 200 ppm or more and a temperature of 100° C. or lower, or to have a water concentration of 80 ppm or more and a temperature of 60° C. or lower, or to have a water concentration of 40 ppm or more and a temperature of 50° C. or lower, or to have a water concentration of 12 ppm or more and a temperature of 30° C. or lower, where these conditions may be determined according to the acetic anhydride concentration, which is typically 1 to 300 ppm, in the acetic acid solution. The residence time of the third acetic acid stream (acetic acid solution) after undergoing any of the first, second, and third acetic anhydride decreasing treatments is typically 1 second or longer, preferably 30 seconds or longer, more preferably 1 minute or longer, more preferably 5 minutes or longer, more preferably 10 minutes or longer, more preferably 30 minutes or longer, more preferably 60 minutes or longer, more preferably 900 minutes or longer, more preferably 1300 minutes or longer, more preferably 1400 minutes or longer, and more preferably 2800 minutes or longer. The term "residence time" of the third acetic acid stream (acetic acid solution) after any of the acetic anhydride decreasing treatments typically refers to a time necessary for the acetic acid solution to reach the ion exchange resin column 7 from a point at which the treatment is performed (e.g., the point at which the line 45 is coupled) in the line 41. A relatively long residence time may be achieved typically by disposing a buffer tank in the midway of the line 41. When a buffer tank is disposed in the midway of the third acetic acid stream zone in the line 41, the "residence time" of the third acetic acid stream after the acetic anhydride decreasing treatment also includes a time during which the acetic acid solution remains in the tank. The configurations on the water concentration, temperature, and residence time in the acetic anhydride decreasing treatments performed on the third acetic acid stream are advantageous for allowing the acetic anhydride hydrolysis reaction to proceed, so as to decrease the acetic anhydride concentration in the third acetic acid stream (acetic acid solution).

The first, second, and third acetic anhydride decreasing treatments, when performed on the third acetic acid stream, preferably allow a catalyst for promoting acetic anhydride hydrolysis to be present in the third acetic acid stream (acetic acid solution). For example, the first, second, and third acetic anhydride decreasing treatments, when performed on the third acetic acid stream, may allow at least one substance selected from Broensted acids, Lewis acids, and corrodible metals to be present in the third acetic acid stream, where these substances are capable of functionally promoting acetic anhydride hydrolysis. In the embodiment, a solution containing such a catalyst to be used can be added through the line 45, which is a supply line, to the third acetic acid stream in the line 41. The catalyst in the acetic acid solution may be present in an amount of preferably 0.01 to 10000 ppm. From the viewpoint of offering sufficient catalysis, the catalyst in the acetic acid solution may be present in an amount of preferably 0.1 ppm or more, more preferably 1 ppm or more, and furthermore preferably 10 ppm or more. When the first, second, and third acetic anhydride decreasing treatments performed on the third acetic acid stream employ a catalyst, the acetic acid solution may have a temperature of typically 180° C. or lower, preferably 170° C. or lower, more preferably 160° C. or lower, more preferably 140° C. or lower, more preferably 120° C. or lower, and more preferably 40° C. or lower. When the first, second, and third acetic anhydride decreasing treatments performed on the third acetic acid stream employ a catalyst, the residence time of the acetic acid solution may be typically 1 second or longer, preferably 10 seconds or longer, more preferably 30 seconds or longer, and more preferably 1 minute or longer. When the first, second, and third acetic anhydride decreasing treatments performed on the third acetic acid stream employ a catalyst, the catalyst can offer its catalytic function in an acetic acid stream until it is removed in the course of acetic acid purification process by the working of the acetic acid production equipment X.

The ion exchange resin column 7 is a unit with which the adsorption/removal step is performed. The adsorption/removal step is the step of removing, via adsorption, mainly alkyl iodides (such as hexyl iodide) from the third acetic acid stream to further purify acetic acid, where the third acetic acid stream is continuously introduced into the ion exchange resin column 7. The ion exchange resin column 7 is packed with an ion exchange resin capable of adsorbing alkyl iodides, where the ion exchange resin forms an ion exchange resin bed in the column. Non-limiting examples of the ion exchange resin include cation-exchange resins in which part of leaving protons in exchange groups such as sulfonic groups, carboxy groups, and phosphonate groups is replaced with a metal such as silver and/or copper. In the adsorption/removal step, the third acetic acid stream (liquid) passes through the interior of the ion exchange resin column 7 typically packed with the ion exchange resin, and, during the passing process, impurities such as alkyl iodides are adsorbed by the ion exchange resin and thereby removed from the third acetic acid stream. In the ion exchange resin column 7 during the adsorption/removal step, the inside temperature is typically 18° C. to 100° C., and the acetic acid stream passes through the column at a flow rate of typically 3 to 15 bed volume per hour.

Into the ion exchange resin column 7, the third acetic acid stream (liquid) from the distillation column 6 is continuously introduced. At the ion exchange resin column 7, a fourth acetic acid stream is continuously drawn out from a lower end portion of the column to the line 46. The fourth acetic acid stream has a higher acetic acid concentration as compared with the third acetic acid stream. Specifically, the fourth acetic acid stream is enriched with acetic acid as compared with the third acetic acid stream continuously introduced into the ion exchange resin column 7. The acetic acid concentration in the fourth acetic acid stream is typically 99.9 to 99.999 mass percent, or more, as long as being higher than the acetic acid concentration in the third acetic acid stream. In the production method, the fourth acetic acid stream may be stored in a product tank (not shown).

The acetic acid production equipment X may further include an additional distillation column, which is a unit for subjecting the fourth acetic acid stream from the ion exchange resin column 7 to additional distillation. The additional distillation column, when provided, may include a column selected typically from rectification columns such as plate columns and packed columns. The distillation column, when being a plate column, may typically have 5 to 50 theoretical plates and may have a reflux ratio of typically 0.5 to 3000 according to the number of the theoretical plates. In the interior of the distillation column during the distillation, the column top pressure may be set typically at −195 to 150 kPa (gauge pressure); and the column bottom pressure may be set at a pressure which is higher than the column top pressure and which is typically from −190 to 180 kPa (gauge pressure). In the interior of the distillation column during the distillation, the column top temperature may be set typically at a temperature which is higher than the boiling point of water and lower than the boiling point of acetic acid each at the set column top pressure and which is from 50° C. to 150° C.; and the column bottom temperature may be set typically at a temperature which is higher than the boiling point of acetic acid at the set column bottom pressure and which is from 70° C. to 180° C. The distillation column may perform a treatment on the fourth acetic acid stream from the ion exchange resin column 7 in the following manner.

The fourth acetic acid stream is continuously introduced from the ion exchange resin column 7 through the line 46 into the additional distillation column, which is disposed downstream from the ion exchange resin column 7.

At the distillation column, vapors as an overhead stream containing trace amounts of low-boiling components are continuously drawn out from the column top. The vapors are separated into condensate components and gaseous components by the working of a predetermined condenser. A part of the condensate components is continuously refluxed to the distillation column; and another part (or the remainder) of the condensate components is recycled to the reactor 1. The gaseous components are fed to the scrubber system 8. A bottom liquid containing trace amounts of high-boiling components is drawn out from the bottom of the distillation column and is recycled typically to the second acetic acid stream in the line 32 before being introduced into the distillation column 6. A side stream (liquid), which is a fifth acetic acid stream, is continuously drawn out of the distillation column at a height level between the column top and the column bottom. The fifth acetic acid stream is enriched with acetic acid as compared with the fourth acetic acid stream continuously introduced into the additional distillation column. In an embodiment of the production method, the fifth acetic acid stream may be stored in the product tank (not shown).

The fourth acetic acid stream to be introduced from the ion exchange resin column 7 through the line 46 into the additional distillation column typically includes acetic acid in a concentration of 90 mass percent or more, acetic anhydride, and water. Assume that the fourth acetic acid stream (acetic acid solution) is in such a state that the equilibrium concentration of acetic anhydride is higher than the acetic anhydride concentration. In this case, the fourth acetic acid stream may be subjected to a first acetic anhydride decreasing treatment in the line 46 in a portion upstream from the additional distillation column. The first acetic anhydride decreasing treatment is the treatment of performing at least one of water concentration increasing and temperature lowering so as to bring the acetic acid solution into such a state that the equilibrium concentration of acetic anhydride is lower than the acetic anhydride concentration. In the first acetic anhydride decreasing treatment herein, the acetic acid solution having an acetic acid concentration of 90 mass percent or more and being in such a state that the equilibrium concentration of acetic anhydride is higher than the acetic anhydride concentration is subjected to water concentration increasing, or temperature lowering, or both in combination. The first acetic anhydride decreasing treatment, when performed, brings the high-concentration acetic acid solution in the line 46 in a portion upstream from the additional distillation column into such a state that the equilibrium concentration of acetic anhydride is lower than the acetic anhydride concentration. In the resulting acetic acid solution brought into this state, the acetic anhydride hydrolysis reaction proceeds so that the acetic anhydride concentration in the solution decreases toward or to the equilibrium concentration of acetic anhydride. In an embodiment as above, the acetic acid production method, which is performed with the acetic acid production equipment X, includes the first acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the fourth acetic acid stream (acetic acid solution) to be introduced from the ion exchange resin column 7 through the line 46 into the additional distillation column is in such a state that the equilibrium concentration of acetic anhydride is lower than the acetic anhydride concentration. In this case, the fourth acetic acid stream may be subjected to a second acetic anhydride decreasing treatment in the line 46 in a portion upstream from the additional distillation column. The second acetic anhydride decreasing treatment is the treatment of performing at least one of water concentration increasing and temperature lowering so as to further lower the equilibrium concentration of acetic anhydride. In the second acetic anhydride decreasing treatment herein, the acetic acid solution having an acetic acid concentration of 90 mass percent or more and being in such a state that the equilibrium concentration of acetic anhydride is lower than the acetic anhydride concentration is subjected to water concentration increasing, or temperature lowering, or both in combination. The second acetic anhydride decreasing treatment as above, when performed, brings the high-concentration acetic acid solution into such a state that the equilibrium concentration of acetic anhydride is further lowered in the line 46 in a portion upstream from the additional distillation column. In the resulting acetic acid solution brought into this state, the acetic anhydride hydrolysis reaction tends to proceed so that the acetic anhydride concentration in the solution decreases toward or to the equilibrium concentration of acetic anhydride. In an embodiment as above, the acetic acid production method, which is performed with the acetic acid production equipment X, includes the second acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the fourth acetic acid stream (acetic acid solution) to be introduced from the ion exchange resin column 7 through the line 46 into the additional distillation column is in such a state that the equilibrium concentration of acetic anhydride is lower than the acetic anhydride concentration. In this case, the fourth acetic acid stream may be subjected to a third acetic anhydride decreasing treatment in the line 46 in a portion upstream from the additional distillation column. The third acetic anhydride decreasing treatment is the treatment of performing temperature rising alone or in combination with water concentration increasing, as long as the state is maintained, so as to increase the reaction rate of acetic anhydride hydrolysis. In an acetic acid solution being in such a state that the equilibrium concentration of acetic anhydride is lower than the acetic anhydride concentration, the acetic anhydride concentration has a tendency to decrease, as long as the state is maintained. To promote or enhance the tendency by increasing the reaction rate of acetic anhydride hydrolysis, the third acetic anhydride decreasing treatment herein subjects the acetic acid solution having an acetic acid concentration of 90 mass percent or more and being in such a state that the equilibrium concentration of acetic anhydride is lower than the acetic anhydride concentration to temperature rising alone or in combination with water concentration increasing, while the state is maintained. The temperature rising alone or in combination with water concentration increasing performed on the acetic acid solution kinetically advantageously acts on increase of the reaction rate of acetic anhydride hydrolysis. The third acetic anhydride decreasing treatment as above, when performed, contributes to an increased reaction rate of acetic anhydride hydrolysis in the high-concentration acetic acid solution in the line 46 in a portion upstream from the additional distillation column, while maintaining the equilibrium concentration of acetic anhydride being lower than the acetic anhydride concentration. This promotes the acetic anhydride hydrolysis reaction so that the acetic anhydride concentration in the solution decreases toward or to the equilibrium concentration of acetic anhydride. In an embodiment as above, the acetic acid production method, which is performed with the acetic acid production equipment X, includes the third acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

The water concentration increasing of the fourth acetic acid stream in the first, second, and third acetic anhydride decreasing treatments performed in a portion from the ion exchange resin column 7 to the additional distillation column may be performed by adding water through a predetermined supply line to the fourth acetic acid stream, where the supply line is coupled to a portion of the line 46 upstream from the additional distillation column. The fourth acetic acid stream (acetic acid solution), when in the state brought by any of the first, second, and third acetic anhydride decreasing treatments, may have a water concentration of typically 7 to 2500 ppm. The acetic acid solution is preferably controlled to have a water concentration of 2500 ppm or less. This is preferred for energy saving in removal of water in the acetic acid purification process so as to produce acetic acid with greater efficiency.

The temperature lowering of the fourth acetic acid stream in the first and second acetic anhydride decreasing treatments may be performed using a cooler (not shown) disposed at the line 46. The temperature rising of the fourth acetic acid stream in the third acetic anhydride decreasing treatment may be performed using a heater (not shown) disposed at the line 46. The fourth acetic acid stream (acetic acid solution), when in the state brought by any of the first, second, and third acetic anhydride decreasing treatments, may have a temperature which is equal to or higher than the melting point of acetic acid and which is typically from 17° C. to 180° C.

The fourth acetic acid stream (acetic acid solution), when in the state brought by any of the first, second, and third acetic anhydride decreasing treatments, is preferably controlled to have a water concentration of 2000 ppm or more and a temperature of 180° C. or lower, or to have a water concentration of 1000 ppm or more and a temperature of 170° C. or lower, or to have a water concentration of 500 ppm or more and a temperature of 120° C. or lower, or to have a water concentration of 200 ppm or more and a temperature of 100° C. or lower, or to have a water concentration of 80 ppm or more and a temperature of 60° C. or lower, or to have a water concentration of 40 ppm or more and a temperature of 50° C. or lower, or to have a water concentration of 12 ppm or more and a temperature of 30° C. or lower, where these conditions may be determined according to the acetic anhydride concentration, which is typically 1 to 300 ppm, in the acetic acid solution. The residence time of the fourth acetic acid stream (acetic acid solution) after undergoing any of the first, second, and third acetic anhydride decreasing treatments is typically 1 second or longer, preferably 30 seconds or longer, more preferably 1 minute or longer, more preferably 5 minutes or longer, more preferably 10 minutes or longer, more preferably 30 minutes or longer, more preferably 60 minutes or longer, more preferably 900 minutes or longer, more preferably 1300 minutes or longer, more preferably 1400 minutes or longer, and more preferably 2800 minutes or longer. The term "residence time" of the fourth acetic acid stream (acetic acid solution) after undergoing the acetic anhydride decreasing treatment refers typically to a time for the acetic acid solution to reach the additional distillation column from a point at which the treatment is performed in the line 46. A relatively long residence time may be achieved typically by disposing a buffer tank in the midway of the line 46. When a buffer tank is disposed in the midway of the fourth acetic acid stream zone in the line 46, the "residence time" of the fourth acetic acid stream after undergoing the acetic anhydride decreasing treatment also includes a time during which the acetic acid solution remains in the tank. The configurations on the water concentration, temperature, and residence time in the acetic anhydride decreasing treatments performed on the fourth acetic acid stream are advantageous for allowing the acetic anhydride hydrolysis reaction to proceed and for thereby decreasing the acetic anhydride concentration in the fourth acetic acid stream (acetic acid solution).

The first, second, and third acetic anhydride decreasing treatments, when performed on the fourth acetic acid stream in a portion from the ion exchange resin column 7 to the additional distillation column, preferably allow a catalyst for promoting acetic anhydride hydrolysis to be present in the fourth acetic acid stream (acetic acid solution). For example, the first, second, and third acetic anhydride decreasing treatments may allow at least one substance selected from Broensted acids, Lewis acids, corrodible metals, ion exchange resins, and sulfonic acids to be present in the fourth acetic acid stream, where these substances are capable of functionally promoting acetic anhydride hydrolysis. Non-limiting examples of the sulfonic acids include $RSO_3H$ where R is alkyl; and salts of them. In the embodiment, a solution containing the catalyst to be used may be added to the fourth acetic acid stream in the line 46 through the supply line as described above relating to the water addition to the fourth acetic acid stream in the first, second, and third acetic anhydride decreasing treatments. Assume that ion exchange resin pieces containing a sulfonic acid or another substance flow out of the ion exchange resin column 7, together with the fourth acetic acid stream, to the line 46, where the sulfonic acid or another substance constitutes the exchange groups in the ion exchange resin material in the ion exchange resin column 7. In this case, the ion exchange resin pieces containing the sulfonic acid or another substance may also be used as the catalyst in the embodiment. The catalyst in the acetic acid solution may be present in an amount of preferably 0.01 to 10000 ppm. From the viewpoint of offering sufficient catalysis, the catalyst in the acetic acid solution may be present in an amount of preferably 0.1 ppm or more, more preferably 1 ppm or more, and furthermore preferably 10 ppm or more. Assume that the first, second, and third acetic anhydride decreasing treatments performed on the fourth acetic acid stream in a portion from the ion exchange resin column 7 to the additional distillation column employ a catalyst. In this case, the acetic acid solution may have a temperature of typically 180° C. or lower, preferably 170° C. or lower, more preferably 160° C. or lower, more preferably 120° C. or lower, and more preferably 40° C. or lower. When the first, second, and third acetic anhydride decreasing treatments performed on the fourth acetic acid stream employ a catalyst, the residence time of the acetic acid solution may be typically 1 second or longer, preferably 10 seconds or longer, more preferably 30 seconds or longer, and furthermore preferably 1 minute or longer. When the first, second, and third acetic anhydride decreasing treatments performed on the fourth acetic acid stream employ a catalyst, the catalyst can offer its catalytic function in an acetic acid stream until it is removed in the course of acetic acid purification process by the working of the acetic acid production equipment X.

As described above, a predetermined acetic acid stream from the ion exchange resin column 7, or from the additional distillation column disposed downstream from the ion exchange resin column 7, can be stored in the product tank (not shown) in the acetic acid production equipment X. The acetic acid stream to be introduced into the product tank typically includes acetic acid in a concentration of 90 mass percent or more, acetic anhydride, and water. Assume that this acetic acid stream (acetic acid solution) is in such a state that the equilibrium concentration of acetic anhydride is higher than the acetic anhydride concentration. In this case, the acetic acid stream (acetic acid solution) passing through a product tank inlet line may be subjected to a first acetic anhydride decreasing treatment. The first acetic anhydride decreasing treatment is the treatment of performing at least one of water concentration increasing and temperature lowering to bring the acetic acid solution into such a state that the equilibrium concentration of acetic anhydride is lower than the acetic anhydride concentration. In the first acetic anhydride decreasing treatment herein, the acetic acid solution having an acetic acid concentration of 90 mass percent or more and being in such a state that the equilibrium concentration of acetic anhydride is higher than the acetic anhydride concentration is subjected to water concentration increasing, or temperature lowering, or both in combination. The first acetic anhydride decreasing treatment as above, when performed, brings the acetic acid solution passing through the product tank inlet line into such a state that the equilibrium concentration of acetic anhydride is lower than the acetic anhydride concentration. In the resulting acetic acid solution brought into this state, the acetic anhydride hydrolysis reaction proceeds so that the acetic anhydride concentration in the solution decreases toward or to the equilibrium concentration of acetic anhydride. In an embodiment as above, the acetic acid production method, which is performed with the acetic acid production equipment X, includes the first acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the acetic acid stream (acetic acid solution) to be introduced into the product tank is in such a state that the equilibrium concentration of acetic anhydride is lower than the acetic anhydride concentration. In this case, the acetic acid solution passing through the product tank inlet line may be subjected to a second acetic anhydride decreasing treatment. The second acetic anhydride decreasing treatment is the treatment of performing at least one of water concentration increasing and temperature lowering so as to further lower the equilibrium concentration of acetic anhydride. In the second acetic anhydride decreasing treatment herein, the acetic acid solution having an acetic acid concentration of 90 mass percent or more and being in such a state that the equilibrium concentration of acetic anhydride is lower than the acetic anhydride concentration is subjected to water concentration increasing, or temperature lowering, or both in combination. The second acetic anhydride decreasing treatment as above, when perform, brings the high-concentration acetic acid solution passing through the product tank inlet line into such a state that the equilibrium concentration of acetic anhydride is further lowered. In the resulting acetic acid solution brought into this state, the acetic anhydride hydrolysis reaction tends to proceed so that the acetic anhydride concentration in the solution decreases toward or to the equilibrium concentration of acetic anhydride. In an embodiment as above, the acetic acid production method, which is performed with the acetic acid production equipment X, includes the second acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

Assume that the acetic acid stream (acetic acid solution) to be introduced into the product tank is in such a state that the equilibrium concentration of acetic anhydride is lower than the acetic anhydride concentration. In this case, the acetic acid solution passing through the product tank inlet line may be subjected to a third acetic anhydride decreasing treatment. The third acetic anhydride decreasing treatment is the treatment of performing temperature rising alone or in combination with water concentration increasing, as long as the state is maintained, so as to increase the reaction rate of acetic anhydride hydrolysis. In the third acetic anhydride decreasing treatment herein, the acetic acid solution having an acetic acid concentration of 90 mass percent or more and being in such a state that the equilibrium concentration of acetic anhydride is lower than the acetic anhydride concentration is subjected to temperature rising alone or in combination with water concentration increasing, while the state is maintained. The temperature rising alone or in combination with water concentration increasing on the acetic acid solution kinetically advantageously acts on increase of the reaction rate of acetic anhydride hydrolysis. The third acetic anhydride decreasing treatment as above, when performed, contributes to an increased reaction rate of acetic anhydride hydrolysis while maintaining the equilibrium concentration of acetic anhydride being lower than the acetic anhydride concentration in the high-concentration acetic acid solution passing through the product tank inlet line. This promotes the acetic anhydride hydrolysis reaction so that the acetic anhydride concentration in the solution decreases toward or to the equilibrium concentration of acetic anhydride. In an embodiment as above, the acetic acid production method, which is performed with the acetic acid production equipment X, includes the third acetic anhydride decreasing treatment in the course of yielding an acetic acid product. This configuration is suitable for decreasing the acetic anhydride concentration in the acetic acid product obtained by the method and is therefore suitable for yielding such a high-purity acetic acid product.

The water concentration increasing of the acetic acid stream passing through the product tank inlet line in the first, second, and third acetic anhydride decreasing treatments may be performed by adding water through a predetermined supply line to the acetic acid stream passing through the product tank inlet line. The amount of water to be added may be determined typically on the basis of chemical composition analysis of a specimen sampled from the acetic acid stream passing through the product tank inlet line. The acetic acid stream (acetic acid solution) in the product tank inlet line, when in the state brought by any of the first, second, and third acetic anhydride decreasing treatments, may have a water concentration of typically 7 to 3000 ppm, preferably 50 to 2000 ppm, more preferably 100 to 1500 ppm, and furthermore preferably 200 to 1000 ppm.

The temperature lowering of the acetic acid stream passing through the product tank inlet line in the first and second acetic anhydride decreasing treatments may be performed using a cooler or a condenser disposed at the product tank inlet line. The temperature rising of the acetic acid stream in the product tank inlet line in the third acetic anhydride decreasing treatment may be performed using a heater disposed at the product tank inlet line. The acetic acid stream (acetic acid solution) in the product tank inlet line, when in the state brought by any of the first, second, and third acetic anhydride decreasing treatments, may have a temperature which is equal to or higher than the melting point of acetic acid and which is typically from 17° C. to 180° C.

The acetic acid stream (acetic acid solution) in the product tank inlet line, when in the state brought by any of the first, second, and third acetic anhydride decreasing treatments, is preferably controlled to have a water concentration of 2000 ppm or more and a temperature of 180° C. or lower, or to have a water concentration of 1000 ppm or more and a temperature of 170° C. or lower, or to have a water concentration of 500 ppm or more and a temperature of 120° C. or lower, or to have a water concentration of 200 ppm or more and a temperature of 100° C. or lower, or to have a water concentration of 80 ppm or more and a temperature of 60° C. or lower, or to have a water concentration of 40 ppm or more and a temperature of 50° C. or lower, or to have a water concentration of 12 ppm or more and a temperature of 30° C. or lower, where these conditions may be determined according to the acetic anhydride concentration, which is typically 1 to 300 ppm, in the acetic acid solution. The residence time of the acetic acid stream (acetic acid solution) in the product tank inlet line after any of the first, second, and third acetic anhydride decreasing treatments is typically 1 second or longer, preferably 30 seconds or longer, more preferably 1 minute or longer, more preferably 5 minutes or longer, more preferably 10 minutes or longer, more preferably 30 minutes or longer, more preferably 60 minutes or longer, more preferably 900 minutes or longer, more preferably 1300 minutes or longer, more preferably 1400 minutes or longer, and more preferably 2800 minutes or longer. As used herein, the term "residence time" of the acetic acid stream after any of the first, second, and third acetic anhydride decreasing treatments in a portion between the additional distillation column and the product tank, where the additional distillation column is disposed downstream from the ion exchange resin column 7, refers typically to a time for the acetic acid solution to travel from a point at which the treatment is performed in the product tank inlet line (the point at which the supply line is coupled) and to be retrieved as an acetic acid product from the product tank. The "residence time" also includes a time during which the acetic acid solution still remains in the product tank. These configurations are advantageous for allowing the acetic anhydride hydrolysis reaction to proceed and for thereby decreasing the acetic anhydride concentration in the acetic acid solution retrieved as the acetic acid product from the product tank.

The acetic acid production method continuously subjects acetic acid formed in the reactor 1 to purification steps in the acetic acid production equipment X as above. The purification steps include not only purifications in the distillation columns 3 and 5, but also purifications in the distillation column 6 and the ion exchange resin column 7, or purifications in the distillation column 6, the ion exchange resin column 7, and the additional distillation column. This acetic acid production method is advantageous for achieving high purity of the resulting acetic acid product. The acetic anhydride concentration of an acetic acid stream passing through the acetic acid production equipment X may vary depending on the temperature condition and pressure condition under which the acetic acid stream is placed, and on the composition of the acetic acid stream. With this method, an acetic acid stream or acetic acid solution underwent purification to a relatively high degree through the distillation column 3 and the distillation column 5 is subjected to any of the first, second, and third acetic anhydride decreasing treatments. These configurations are suitable for decreasing the acetic anhydride concentration in the resulting acetic acid product and is thereby suitable for yielding such a high-purity acetic acid product. As described above, the acetic acid production method is suitable for yielding a high-purity acetic acid product.

EXAMPLES

The present invention will be illustrated in further detail with reference to several examples below. It should be noted, however, that the examples are by no means intended to limit the scope of the present invention.

Examples 1 to 24

Each 500 ml of acetic acid solutions according to Examples 1 to 24 were prepared, where the acetic acid solutions had concentrations given in the columns of "Before test" relating to Examples 1 to 24 in Tables 1 to 4. The acetic acid solutions according to Examples 8 and 21 to 24 have compositions equivalent to the compositions of acetic acid products. The acetic acid solutions according to Examples 14 to 17 were prepared by adding AMBERLYST (supplied by Organo Corporation), which is a cation-exchange resin, to acetic acid solutions having compositions equivalent to the compositions of acetic acid products. The acetic acid solutions according to the examples were subjected to reaction tests. The temperature conditions, pressure conditions, and holding time periods in the reaction tests of the acetic acid solutions according to the examples are as given in Tables 1 to 4, where each pressure is indicated as "atmospheric pressure" or indicated by a numerical value in kilopascal (kPa) (gauge pressure). The acetic acid solutions according to Examples 1 to 4 were subjected to reaction tests in a 500-ml flask in a nitrogen atmosphere under complete reflux conditions. The acetic acid solutions according to Examples 5, 6, 19, and 20 were subjected to reaction tests in a 500-ml pressure-tight case of an autoclave in a nitrogen atmosphere under hermetically sealed conditions. The acetic acid solutions according to Examples 7 to 18 and 21 to 24 were subjected to reaction tests in a 500-ml flask in a nitrogen atmosphere under hermetically sealed conditions. The acetic acid solutions after undergoing the reaction tests were cooled down to 20° C. by allowing the same to pass through a glass condenser within about 10 seconds from the end of the holding time (Examples 1 to 4, 7 to 18, 21 to 24), or from completion of pressure release of the autoclave after the end of the holding time (Examples 5, 6, 19, and 20). After cooling, chemical compositions of the acetic acid solutions were analyzed. The results of chemical composition analyses on the examples are presented in "After test" in Table 1 (Examples 1 to 7), Table 2 (Examples 8 to 14), Table 3 (Examples 15 to 21), and Table 4 (Examples 22 to 24).

Comparative Examples 1 to 9

Each 500 ml of acetic acid solutions according to Comparative Examples 1 to 9 were prepared, where the acetic acid solutions had concentrations given in "Before test" of Comparative Examples 1 to 9 in Tables 4 and 5. The acetic acid solutions according to the comparative examples were subjected to reaction tests. The temperature conditions, pressure conditions, and holding time periods in the reaction tests of the acetic acid solutions according to the comparative examples are as given in Tables 4 and 5, where each pressure is indicated as "atmospheric pressure" or indicated by a numerical value in kilopascal (kPa) (gauge pressure). The acetic acid solutions according to Comparative Examples 1 to 4 and 7 to 9 were subjected to reaction tests in a 500-ml flask in a nitrogen atmosphere under complete reflux conditions. The acetic acid solutions according to Comparative Examples 5 and 6 were subjected to reaction tests in a 500-ml pressure-tight case of an autoclave in a nitrogen atmosphere under hermetically sealed conditions. The acetic acid solutions after undergoing the reaction tests were cooled down to 20° C. by allowing the same to pass through a glass condenser within about 10 seconds from the end of the holding time (Comparative Examples 1 to 4 and 7 to 9), or from completion of pressure release of the autoclave after the end of the holding time (Comparative Examples 5 and 6). After cooling, the chemical compositions of the acetic acid solutions were analyzed. The results of the chemical composition analyses are presented as data in "After test" in Table 4 (Comparative Examples 1 to 3) and Table 5 (Comparative Examples 4 to 9).

Evaluations

Comparisons in compositions of Examples 1 to 24 between before and after testing reveal that the acetic anhydride concentrations decreased after testing. This demonstrates that the acetic acid solutions having the compositions before testing according to Examples 1 to 24 are each in such a state that the equilibrium concentration of acetic anhydride is lower than the acetic anhydride concentration of 260 ppm (Examples 1 to 17, 19, and 20) or than the acetic anhydride concentration of 110 ppm (Examples 18 and 21 to 24) under the specified temperature and pressure conditions.

For example, the data demonstrate that the acetic acid solutions having the compositions before testing according to Examples 1 to 3 are each in such a state that the equilibrium concentration of acetic anhydride is lower than the acetic anhydride concentration of 260 ppm at a temperature of 118° C. and a pressure of atmospheric pressure. Comparisons among Examples 1 to 3, which are identical in water concentration and acetic anhydride concentration in the compositions before testing, demonstrate that the acetic anhydride concentration after testing decreases with a longer holding time in the reaction test.

Comparisons between Examples 3 and 4 demonstrate that the acetic anhydride concentration tends to decrease with an increasing water concentration in the compositions before testing. Comparisons among Examples 4 to 6 demonstrate that the acetic anhydride concentration tends to decrease with a decreasing temperature of the reaction test.

As given in Tables 1 and 2, the compositions before testing according to Examples 7 and 8 are identical in water concentration and acetic anhydride concentration, but significantly different in concentrations of propionic acid, methyl acetate, formic acid, hydrogen iodide, iodine ion, methyl iodide, hexyl iodide, and potassium. The reaction tests performed on Examples 7 and 8 are identical in temperature condition (40° C.), pressure condition (atmospheric pressure), and holding time (240 min). Comparisons between Examples 7 and 8 give understanding that the differences in compositions or concentrations between the acetic acid solutions having the compositions before testing according to Examples 7 and 8 do not significantly affect the reaction rate of acetic anhydride hydrolysis under conditions at a temperature of 40° C. and a pressure of atmospheric pressure.

Comparisons between Examples 9 and 10 demonstrate that the acetic anhydride concentration tends to decrease with an increasing water concentration in the compositions before testing. Comparisons between Examples 9 and 10 and Examples 7 and 8 demonstrate that the acetic anhydride concentration can be significantly decreased by ensuring a sufficiently long holding time in the reaction test, even when the reaction test is performed at a relatively low temperature of 40° C.

Comparisons between Examples 11 and 12 demonstrate that the acetic anhydride concentration tends to decrease with increasing concentrations of metals or corrodible metals (Fe, Ni, Cr, Mo, Mn, and Li) which promote the acetic anhydride hydrolysis reaction. Comparisons among Examples 13 to 17 demonstrate that the acetic anhydride concentration tends to decrease with an increasing concentration of the cation-exchange resin (AMBERLYST) which promotes the acetic anhydride hydrolysis reaction.

The results of Examples 18, 21, and 22 demonstrate that the acetic anhydride concentration can be significantly decreased by ensuring a sufficiently long holding time in the reaction tests, even when the reaction tests are performed at a relatively low temperature of 28° C. (Example 18) or 17° C. (Examples 21 and 22), and the water concentration before testing is relatively low of 12 ppm. At a holding time in the reaction test of 1300 min, Example 18 offers more decrease in acetic anhydride concentration as compared with Example 21, where the reaction test temperature is higher in Example 18 than in Example 21. At a reaction test temperature of 17° C., Example 22 offers more decrease in acetic anhydride concentration as compared with Example 21, where the holding time in the reaction test is longer in Example 22 than in Example 21. The results in Examples 18, 21, and 22 indicate that the acetic anhydride hydrolysis reaction proceeds slower, but the equilibrium concentration of acetic anhydride is lower in the sample undergoing the reaction test at a temperature of 17° C. as compared with the sample undergoing the reaction test at a temperature of 28° C.

Comparisons between Example 19 and Example 5 demonstrate that the pressure condition in the reaction tests does not significantly affect the degree of decrease in acetic anhydride concentration. The results of Example 20 demonstrate that the acetic anhydride concentration can be decreased by employing a sufficiently high water concentration in the composition before testing, even when the reaction test is performed at a relatively high temperature of 170° C.

The results of Example 23 demonstrate that the acetic anhydride concentration can be significantly decreased by adjusting the water concentration in the composition before testing to a level of at least 40 ppm at an acetic anhydride concentration of 110 ppm, even when the reaction test is performed at a relatively high temperature of 50° C. The results of Example 24 demonstrate that the acetic anhydride concentration can be significantly decreased by adjusting the water concentration in the composition before testing to a level of at least 80 ppm at an acetic anhydride concentration of 110 ppm, even when the reaction test is performed at a relatively high temperature of 60° C. On Examples 23 and 24, it has been verified that the acetic anhydride concentration and the water concentration did not vary even at a holding time in the reaction test of longer than 60 min (Example 23), or longer than 30 min (Example 24). Accordingly, it can be evaluated that the acetic anhydride concentration reaches the equilibrium concentration of acetic anhydride in each of the acetic acid solutions having the compositions after testing according to Examples 23 and 24. It has been verified that an acetic acid solution having a composition before testing identical to that in Example 23, except having a water concentration of 12 ppm, had an acetic anhydride concentration increased from 110 ppm under temperature and pressure conditions identical to those in Example 23. It has also been verified that an acetic acid solution having a composition before testing identical to that in Example 24, except for having a water concentration of 12 ppm, had an acetic anhydride concentration increased from 110 ppm under temperature and pressure conditions identical to those in Example 24.

In contrast, comparisons in compositions of Comparative Examples 1 to 9 between before and after testing reveal that the acetic anhydride concentrations increase after testing. This demonstrates that the acetic acid solutions having the compositions before testing according to Comparative Examples 1 to 9 are each in such a state that the equilibrium concentration of acetic anhydride is higher than the acetic anhydride concentration of 10 ppm (Comparative Examples 1 and 7 to 9) or than the acetic anhydride concentration of 260 ppm (Comparative Examples 2 to 6) under the specified temperature and pressure conditions.

For example, the data demonstrate that the acetic acid solutions having the compositions before testing according to Comparative Example 1 and Comparative Examples 7 to 9 are each in such a state that the equilibrium concentration of acetic anhydride is higher than the acetic anhydride concentration of 10 ppm at a temperature of 118° C. and a pressure of atmospheric pressure. Comparative Example 1 and Comparative Examples 7 to 9 are identical in water concentration (500 ppm) and acetic anhydride concentration (10 ppm) in the compositions before testing. Comparisons between Comparative Example 1 and Comparative Examples 7 to 9 demonstrate that increase in acetic anhydride concentration is restrained in the sample (Comparative Example 1) containing no catalytic component in the acetic acid solution, as compared with the samples (Comparative Examples 7 to 9) containing any of catalytic components (Fe, Ni, Cr, Mo, Mn, Li, and AMBERLYST) in the acetic acid solutions.

Comparative Examples 2 and 3 are identical in water concentration and acetic anhydride concentration in the compositions before testing. Comparisons between these comparative examples demonstrate that the acetic anhydride concentration more increases in the sample (Comparative Example 3) where the reaction test is performed for a longer holding time of 30 min, as compared with the sample (Comparative Example 2) where the reaction test is performed for 1 minute. Comparative Examples 3 and 4 are identical in temperature condition, pressure condition, and holding time period of the reaction tests and in acetic anhydride concentration in the compositions before testing. Comparisons between these comparative examples demonstrate that the acetic anhydride concentration more increases in the sample (Comparative Example 4) where the reaction test begins at a lower water concentration of 50 ppm, as compared with the sample (Comparative Example 3) where the reaction test begins at a water concentration of 100 ppm.

Comparative Examples 3, 5, and 6 are identical in water concentration and acetic anhydride concentration in the composition before testing, and in holding time in the reaction test. Comparisons among these comparative examples demonstrate that the acetic anhydride concentration tends to increases more with an increasing temperature of the reaction test.

Example 3 and Comparative Example 1 are different only in acetic anhydride concentration in the compositions before testing, as given in Tables 1 and 4. In contrast, Example 3 and Comparative Example 1 are identical in temperature condition (118° C.), pressure condition (atmospheric pressure), and holding time (30 min) in the reaction tests. Comparisons in compositions of Example 3 between before and after testing reveal that the acetic anhydride concentration decreases after testing. This demonstrates that the acetic acid solution having the composition before testing according to Example 3 is in such a state that the equilibrium concentration of acetic anhydride is lower than the acetic anhydride concentration of 260 ppm at a temperature of 118° C. and a pressure of atmospheric pressure. In contrast, comparisons in compositions of Comparative Example 1 between before and after testing reveal that the acetic anhydride concentration increases after testing. This demonstrates that the acetic acid solution having the composition before testing according to Comparative Example 1 is in such a state that the equilibrium concentration of acetic anhydride is higher than the acetic anhydride concentration of 10 ppm at a temperature of 118° C. and a pressure of atmospheric pressure. The results of Example 3 and Comparative Example 1 indicate as follows. An acetic acid solution, when having a relatively high acetic anhydride concentration, tends to have a decreased acetic anhydride concentration effectively by holding or residing at a high temperature. However, assume that an acetic acid solution resides at a high temperature and subsequently is held in a low temperature region for a predetermined time under the catalysis of, or without the catalysis of, a catalyst so as to have a decreased acetic anhydride concentration, and is then subjected to temperature rising. In this case, the acetic acid solution may have an increased acetic anhydride concentration.

TABLE 1

|  | Example 1 | | Example 2 | | Example 3 | | Example 4 | |
| --- | --- | --- | --- | --- | --- | --- | --- | --- |
|  | Before test | After test | Before test | After test | Before test | After test | Before test | After test |
| Temperature (° C.) | 118 | | 118 | | 118 | | 118 | |
| Pressure (kPa) | atmospheric pressure | | atmospheric pressure | | atmospheric pressure | | atmospheric pressure | |
| Holding time (min) | 0.5 | | 1 | | 30 | | 30 | |
| Water (ppm) | 500 | 495 | 500 | 490 | 500 | 470 | 1000 | 962 |
| Acetic anhydride (ppm) | 260 | 240 | 260 | 220 | 260 | 88 | 260 | 44 |
| Propionic acid (ppm) | 98 | 97 | 98 | 95 | 98 | 95 | 98 | 95 |
| Methyl acetate (ppm) | 5 | 5 | 5 | 4 | 5 | 4 | 5 | 4 |
| Methanol (ppm) | 1> | 1> | 1> | 1> | 1> | 1> | 1> | 1> |
| Formic acid (ppm) | 21 | 19 | 21 | 18 | 21 | 19 | 21 | 18 |
| Hydrogen iodide (ppm) | 210 | 200 | 210 | 195 | 210 | 198 | 210 | 195 |
| Iodine ion (ppb) | 200 | 195 | 200 | 190 | 200 | 193 | 200 | 190 |
| Methyl iodide (ppb) | 5 | 4 | 5 | 4 | 5 | 4 | 5 | 4 |
| Hexyl iodide (ppb) | 8 | 7 | 8 | 8 | 8 | 8 | 8 | 8 |
| Potassium (ppm) | 8 | 8 | 8 | 8 | 8 | 8 | 8 | 9 |

TABLE 1-continued

|  | | | | | | | | |
|---|---|---|---|---|---|---|---|---|
| Fe (ppm) | 0 | 0 | 0 | 0 | 0 | 0 | 0 | 0 |
| Ni (ppm) | 0 | 0 | 0 | 0 | 0 | 0 | 0 | 0 |
| Cr (ppm) | 0 | 0 | 0 | 0 | 0 | 0 | 0 | 0 |
| Mo (ppm) | 0 | 0 | 0 | 0 | 0 | 0 | 0 | 0 |
| Mn (ppm) | 0 | 0 | 0 | 0 | 0 | 0 | 0 | 0 |
| Li (ppm) | 0 | 0 | 0 | 0 | 0 | 0 | 0 | 0 |
| AMBERLYST (ppm) | 0 | 0 | 0 | 0 | 0 | 0 | 0 | 0 |
| Acetic acid | remainder | remainder | remainder | remainder | remainder | remainder | remainder | remainder |

|  | Example 5 | | Example 6 | | Example 7 | |
|---|---|---|---|---|---|---|
|  | Before test | After test | Before test | After test | Before test | After test |
| Temperature (° C.) | 140 | | 160 | | 40 | |
| Pressure (kPa) | 200 | | 200 | | atmospheric pressure | |
| Holding time (min) | 30 | | 30 | | 240 | |
| Water (ppm) | 1000 | 971 | 1000 | 991 | 500 | 497 |
| Acetic anhydride (ppm) | 260 | 95 | 260 | 208 | 260 | 245 |
| Propionic acid (ppm) | 98 | 95 | 98 | 95 | 98 | 95 |
| Methyl acetate (ppm) | 5 | 4 | 5 | 4 | 5 | 4 |
| Methanol (ppm) | 1> | 1> | 1> | 1> | 1> | 1> |
| Formic acid (ppm) | 21 | 18 | 21 | 13 | 21 | 20 |
| Hydrogen iodide (ppm) | 210 | 195 | 210 | 190 | 210 | 205 |
| Iodine ion (ppb) | 200 | 190 | 200 | 180 | 200 | 199 |
| Methyl iodide (ppb) | 5 | 4 | 5 | 4 | 5 | 5 |
| Hexyl iodide (ppb) | 8 | 8 | 8 | 8 | 8 | 8 |
| Potassium (ppm) | 8 | 7 | 8 | 6 | 8 | 7 |
| Fe (ppm) | 0 | 0 | 0 | 0 | 0 | 0 |
| Ni (ppm) | 0 | 0 | 0 | 0 | 0 | 0 |
| Cr (ppm) | 0 | 0 | 0 | 0 | 0 | 0 |
| Mo (ppm) | 0 | 0 | 0 | 0 | 0 | 0 |
| Mn (ppm) | 0 | 0 | 0 | 0 | 0 | 0 |
| Li (ppm) | 0 | 0 | 0 | 0 | 0 | 0 |
| AMBERLYST (ppm) | 0 | 0 | 0 | 0 | 0 | 0 |
| Acetic acid | remainder | remainder | remainder | remainder | remainder | remainder |

TABLE 2

|  | Example 8 | | Example 9 | | Example 10 | | Example 11 | |
|---|---|---|---|---|---|---|---|---|
|  | Before test | After test | Before test | After test | Before test | After test | Before test | After test |
| Temperature (° C.) | 40 | | 40 | | 40 | | 40 | |
| Pressure (kPa) | atmospheric pressure | | atmospheric pressure | | atmospheric pressure | | atmospheric pressure | |
| Holding time (min) | 240 | | 900 | | 900 | | 30 | |
| Water (ppm) | 500 | 499 | 500 | 463 | 200 | 172 | 500 | 479 |
| Acetic anhydride (ppm) | 260 | 252 | 260 | 50 | 260 | 100 | 260 | 140 |
| Propionic acid (ppm) | 95 | 95 | 98 | 95 | 98 | 95 | 98 | 95 |
| Methyl acetate (ppm) | 1 | 1 | 5 | 4 | 5 | 4 | 5 | 4 |
| Methanol (ppm) | 1> | 1> | 1> | 1> | 1> | 1> | 1> | 1> |
| Formic acid (ppm) | 10 | 10 | 21 | 11 | 21 | 20 | 21 | 20 |
| Hydrogen iodide (ppm) | 0.3 | 0.3 | 210 | 191 | 210 | 205 | 210 | 205 |
| Iodine ion (ppb) | 0.4 | 0.4 | 200 | 183 | 200 | 199 | 200 | 199 |
| Methyl iodide (ppb) | 0.5 | 0.5 | 5 | 4 | 5 | 5 | 5 | 5 |
| Hexyl iodide (ppb) | 1> | 1> | 8 | 8 | 8 | 8 | 8 | 8 |
| Potassium (ppm) | 0 | 0 | 8 | 8 | 8 | 9 | 8 | 7 |
| Fe (ppm) | 0 | 0 | 0 | 0 | 0 | 0 | 1 | 1 |
| Ni (ppm) | 0 | 0 | 0 | 0 | 0 | 0 | 1 | 1 |
| Cr (ppm) | 0 | 0 | 0 | 0 | 0 | 0 | 1 | 1 |
| Mo (ppm) | 0 | 0 | 0 | 0 | 0 | 0 | 1 | 1 |
| Mn (ppm) | 0 | 0 | 0 | 0 | 0 | 0 | 1 | 1 |
| Li (ppm) | 0 | 0 | 0 | 0 | 0 | 0 | 1 | 1 |
| AMBERLYST (ppm) | 0 | 0 | 0 | 0 | 0 | 0 | 0 | 0 |
| Acetic acid | remainder | remainder | remainder | remainder | remainder | remainder | remainder | remainder |

|  | Example 12 | | Example 13 | | Example 14 | |
|---|---|---|---|---|---|---|
|  | Before test | After test | Before test | After test | Before test | After test |
| Temperature (° C.) | 40 | | 40 | | 40 | |
| Pressure (kPa) | atmospheric pressure | | atmospheric pressure | | atmospheric pressure | |
| Holding time (min) | 30 | | 30 | | 30 | |
| Water (ppm) | 500 | 489 | 500 | 481 | 500 | 475 |

TABLE 2-continued

|  |  |  |  |  |  |  |
|---|---|---|---|---|---|---|
| Acetic anhydride (ppm) | 260 | 195 | 260 | 150 | 260 | 120 |
| Propionic acid (ppm) | 98 | 95 | 98 | 95 | 95 | 95 |
| Methyl acetate (ppm) | 5 | 4 | 5 | 4 | 1 | 1 |
| Methanol (ppm) | 1> | 1> | 1> | 1> | 1> | 1> |
| Formic acid (ppm) | 21 | 20 | 21 | 20 | 10 | 10 |
| Hydrogen iodide (ppm) | 210 | 205 | 210 | 205 | 0.3 | 0.3 |
| Iodine ion (ppb) | 200 | 199 | 200 | 199 | 0.4 | 0.4 |
| Methyl iodide (ppb) | 5 | 5 | 5 | 5 | 0.5 | 0.5 |
| Hexyl iodide (ppb) | 8 | 8 | 8 | 8 | 1> | 1> |
| Potassium (ppm) | 8 | 7 | 8 | 7 | 0 | 0 |
| Fe (ppm) | 0.1 | 0.1 | 0 | 0 | 0 | 0 |
| Ni (ppm) | 0.1 | 0.1 | 0 | 0 | 0 | 0 |
| Cr (ppm) | 0.1 | 0.1 | 0 | 0 | 0 | 0 |
| Mo (ppm) | 0.1 | 0.1 | 0 | 0 | 0 | 0 |
| Mn (ppm) | 0.1 | 0.1 | 0 | 0 | 0 | 0 |
| Li (ppm) | 0.1 | 0.1 | 0 | 0 | 0 | 0 |
| AMBERLYST (ppm) | 0 | 0 | 1 | 1 | 10 | 10 |
| Acetic acid | remainder | remainder | remainder | remainder | remainder | remainder |

TABLE 3

|  | Example 15 | | Example 16 | | Example 17 | | Example 18 | |
|---|---|---|---|---|---|---|---|---|
|  | Before test | After test | Before test | After test | Before test | After test | Before test | After test |
| Temperature (° C.) | 40 | | 40 | | 40 | | 28 | |
| Pressure (kPa) | atmospheric pressure | | atmospheric pressure | | atmospheric pressure | | atmospheric pressure | |
| Holding time (min) | 10 | | 5 | | 1 | | 1300 | |
| Water (ppm) | 500 | 477 | 500 | 468 | 500 | 467 | 12 | 7 |
| Acetic anhydride (ppm) | 260 | 130 | 260 | 80 | 260 | 75 | 110 | 79 |
| Propionic acid (ppm) | 95 | 95 | 95 | 95 | 95 | 95 | 95 | 95 |
| Methyl acetate (ppm) | 1 | 1 | 1 | 1 | 1 | 1 | 1 | 1 |
| Methanol (ppm) | 1> | 1> | 1> | 1> | 1> | 1> | 1> | 1> |
| Formic acid (ppm) | 10 | 10 | 10 | 10 | 10 | 10 | 10 | 10 |
| Hydrogen iodide (ppm) | 0.3 | 0.3 | 0.3 | 0.3 | 0.3 | 0.3 | 0.3 | 0.2 |
| Iodine ion (ppb) | 0.4 | 0.4 | 0.4 | 0.4 | 0.4 | 0.4 | 0.4 | 0.4 |
| Methyl iodide (ppb) | 0.5 | 0.5 | 0.5 | 0.5 | 0.5 | 0.5 | 0.5 | 0.3 |
| Hexyl iodide (ppb) | 1> | 1> | 1> | 1> | 1> | 1> | 1> | 1> |
| Potassium (ppm) | 0 | 0 | 0 | 0 | 0 | 0 | 0 | 0 |
| Fe (ppm) | 0 | 0 | 0 | 0 | 0 | 0 | 0 | 0 |
| Ni (ppm) | 0 | 0 | 0 | 0 | 0 | 0 | 0 | 0 |
| Cr (ppm) | 0 | 0 | 0 | 0 | 0 | 0 | 0 | 0 |
| Mo (ppm) | 0 | 0 | 0 | 0 | 0 | 0 | 0 | 0 |
| Mn (ppm) | 0 | 0 | 0 | 0 | 0 | 0 | 0 | 0 |
| Li (ppm) | 0 | 0 | 0 | 0 | 0 | 0 | 0 | 0 |
| AMBERLYST (ppm) | 100 | 100 | 1000 | 1000 | 10000 | 10000 | 0 | 0 |
| Acetic acid | remainder | remainder | remainder | remainder | remainder | remainder | remainder | remainder |

|  | Example 19 | | Example 20 | | Example 21 | |
|---|---|---|---|---|---|---|
|  | Before test | After test | Before test | After test | Before test | After test |
| Temperature (° C.) | 140 | | 170 | | 17 | |
| Pressure (kPa) | 400 | | 200 | | atmospheric pressure | |
| Holding time (min) | 30 | | 30 | | 1300 | |
| Water (ppm) | 1000 | 973 | 2000 | 1990 | 12 | 8 |
| Acetic anhydride (ppm) | 260 | 97 | 260 | 202 | 110 | 84 |
| Propionic acid (ppm) | 98 | 95 | 98 | 95 | 95 | 95 |
| Methyl acetate (ppm) | 5 | 3 | 5 | 3 | 1 | 1 |
| Methanol (ppm) | 1> | 1> | 1> | 1> | 1> | 1> |
| Formic acid (ppm) | 21 | 19 | 21 | 11 | 10 | 10 |
| Hydrogen iodide (ppm) | 210 | 194 | 210 | 188 | 0.3 | 0.2 |
| Iodine ion (ppb) | 200 | 189 | 200 | 179 | 0.4 | 0.4 |
| Methyl iodide (ppb) | 5 | 4 | 5 | 3 | 0.5 | 0.3 |
| Hexyl iodide (ppb) | 8 | 7 | 8 | 7 | 1> | 1> |
| Potassium (ppm) | 8 | 7 | 8 | 6 | 0 | 0 |
| Fe (ppm) | 0 | 0 | 0 | 0 | 0 | 0 |
| Ni (ppm) | 0 | 0 | 0 | 0 | 0 | 0 |
| Cr (ppm) | 0 | 0 | 0 | 0 | 0 | 0 |

TABLE 3-continued

|  | | | | | | |
|---|---|---|---|---|---|---|
| Mo (ppm) | 0 | 0 | 0 | 0 | 0 | 0 |
| Mn (ppm) | 0 | 0 | 0 | 0 | 0 | 0 |
| Li (ppm) | 0 | 0 | 0 | 0 | 0 | 0 |
| AMBERLYST (ppm) | 0 | 0 | 0 | 0 | 0 | 0 |
| Acetic acid | remainder | remainder | remainder | remainder | remainder | remainder |

TABLE 4

| | Example 22 | | Example 23 | | Example 24 | |
|---|---|---|---|---|---|---|
| | Before test | After test | Before test | After test | Before test | After test |
| Temperature (° C.) | 17 | | 50 | | 60 | |
| Pressure (kPa) | atmospheric pressure | | atmospheric pressure | | atmospheric pressure | |
| Holding time (min) | 2800 | | 60 | | 30 | |
| Water (ppm) | 12 | 6 | 40 | 30 | 80 | 70 |
| Acetic anhydride (ppm) | 110 | 73 | 110 | 53 | 110 | 53 |
| Propionic acid (ppm) | 95 | 94 | 95 | 96 | 95 | 94 |
| Methyl acetate (ppm) | 1 | 1 | 1 | 1 | 1 | 1 |
| Methanol (ppm) | 1> | 1> | 1> | 1> | 1> | 1> |
| Formic acid (ppm) | 10 | 10 | 10 | 9 | 10 | 8 |
| Hydrogen iodide (ppm) | 0.3 | 0.3 | 0.3 | 0.2 | 0.3 | 0.3 |
| Iodine ion (ppb) | 0.4 | 0.3 | 0.4 | 0.4 | 0.4 | 0.4 |
| Methyl iodide (ppb) | 0.5 | 0.4 | 0.5 | 0.4 | 0.5 | 0.3 |
| Hexyl iodide (ppb) | 1> | 1> | 1> | 1> | 1> | 1> |
| Potassium (ppm) | 0 | 0 | 0 | 0 | 0 | 0 |
| Fe (ppm) | 0 | 0 | 0 | 0 | 0 | 0 |
| Ni (ppm) | 0 | 0 | 0 | 0 | 0 | 0 |
| Cr (ppm) | 0 | 0 | 0 | 0 | 0 | 0 |
| Mo (ppm) | 0 | 0 | 0 | 0 | 0 | 0 |
| Mn (ppm) | 0 | 0 | 0 | 0 | 0 | 0 |
| Li (ppm) | 0 | 0 | 0 | 0 | 0 | 0 |
| AMBERLYST (ppm) | 0 | 0 | 0 | 0 | 0 | 0 |
| Acetic acid | remainder | remainder | remainder | remainder | remainder | remainder |

| | Comparative Example 1 | | Comparative Example 2 | | Comparative Example 3 | |
|---|---|---|---|---|---|---|
| | Before test | After test | Before test | After test | Before test | After test |
| Temperature (° C.) | 118 | | 118 | | 118 | |
| Pressure (kPa) | atmospheric pressure | | atmospheric pressure | | atmospheric pressure | |
| Holding time (min) | 30 | | 1 | | 30 | |
| Water (ppm) | 500 | 507 | 100 | 80 | 100 | 132 |
| Acetic anhydride (ppm) | 10 | 50 | 260 | 300 | 260 | 442 |
| Propionic acid (ppm) | 98 | 95 | 98 | 95 | 98 | 95 |
| Methyl acetate (ppm) | 5 | 4 | 5 | 4 | 5 | 4 |
| Methanol (ppm) | 1> | 1> | 1> | 1> | 1> | 1> |
| Formic acid (ppm) | 21 | 20 | 21 | 19 | 21 | 18 |
| Hydrogen iodide (ppm) | 210 | 205 | 210 | 198 | 210 | 195 |
| Iodine ion (ppb) | 200 | 199 | 200 | 193 | 200 | 190 |
| Methyl iodide (ppb) | 5 | 5 | 5 | 4 | 5 | 4 |
| Hexyl iodide (ppb) | 8 | 8 | 8 | 8 | 8 | 8 |
| Potassium (ppm) | 8 | 7 | 8 | 8 | 8 | 8 |
| Fe (ppm) | 0 | 0 | 0 | 0 | 0 | 0 |
| Ni (ppm) | 0 | 0 | 0 | 0 | 0 | 0 |
| Cr (ppm) | 0 | 0 | 0 | 0 | 0 | 0 |
| Mo (ppm) | 0 | 0 | 0 | 0 | 0 | 0 |
| Mn (ppm) | 0 | 0 | 0 | 0 | 0 | 0 |
| Li (ppm) | 0 | 0 | 0 | 0 | 0 | 0 |
| AMBERLYST (ppm) | 0 | 0 | 0 | 0 | 0 | 0 |
| Acetic acid | remainder | remainder | remainder | remainder | remainder | remainder |

TABLE 5

| | Comparative Example 4 | | Comparative Example 5 | | Comparative Example 6 | |
|---|---|---|---|---|---|---|
| | Before test | After test | Before test | After test | Before test | After test |
| Temperature (° C.) | 118 | | 140 | | 160 | |
| Pressure (kPa) | atmospheric pressure | | 200 | | 200 | |

TABLE 5-continued

|  | | | | | | |
|---|---|---|---|---|---|---|
| Holding time (min) | 30 | | 30 | | 30 | |
| Water (ppm) | 50 | 160 | 100 | 221 | 100 | 767 |
| Acetic anhydride (ppm) | 260 | 884 | 260 | 945 | 260 | 4039 |
| Propionic acid (ppm) | 98 | 95 | 98 | 95 | 98 | 95 |
| Methyl acetate (ppm) | 5 | 4 | 5 | 4 | 5 | 4 |
| Methanol (ppm) | 1> | 1> | 1> | 1> | 1> | 1> |
| Formic acid (ppm) | 21 | 18 | 21 | 13 | 21 | 11 |
| Hydrogen iodide (ppm) | 210 | 195 | 210 | 190 | 210 | 191 |
| Iodine ion (ppb) | 200 | 190 | 200 | 180 | 200 | 183 |
| Methyl iodide (ppb) | 5 | 4 | 5 | 4 | 5 | 4 |
| Hexyl iodide (ppb) | 8 | 8 | 8 | 8 | 8 | 8 |
| Potassium (ppm) | 8 | 9 | 8 | 6 | 8 | 8 |
| Fe (ppm) | 0 | 0 | 0 | 0 | 0 | 0 |
| Ni (ppm) | 0 | 0 | 0 | 0 | 0 | 0 |
| Cr (ppm) | 0 | 0 | 0 | 0 | 0 | 0 |
| Mo (ppm) | 0 | 0 | 0 | 0 | 0 | 0 |
| Mn (ppm) | 0 | 0 | 0 | 0 | 0 | 0 |
| Li (ppm) | 0 | 0 | 0 | 0 | 0 | 0 |
| AMBERLYST (ppm) | 0 | 0 | 0 | 0 | 0 | 0 |
| Acetic acid | remainder | remainder | remainder | remainder | remainder | remainder |

|  | Comparative Example 7 | | Comparative Example 8 | | Comparative Example 9 | |
|---|---|---|---|---|---|---|
|  | Before test | After test | Before test | After test | Before test | After test |
| Temperature (° C.) | 118 | | 118 | | 118 | |
| Pressure (kPa) | atmospheric pressure | | atmospheric pressure | | atmospheric pressure | |
| Holding time (min) | 30 | | 30 | | 30 | |
| Water (ppm) | 500 | 514 | 500 | 509 | 500 | 514 |
| Acetic anhydride (ppm) | 10 | 88 | 10 | 60 | 10 | 92 |
| Propionic acid (ppm) | 98 | 95 | 98 | 95 | 98 | 95 |
| Methyl acetate (ppm) | 5 | 4 | 5 | 4 | 5 | 4 |
| Methanol (ppm) | 1> | 1> | 1> | 1> | 1> | 1> |
| Formic acid (ppm) | 21 | 20 | 21 | 20 | 21 | 20 |
| Hydrogen iodide (ppm) | 210 | 205 | 210 | 205 | 210 | 205 |
| Iodine ion (ppb) | 200 | 199 | 200 | 199 | 200 | 199 |
| Methyl iodide (ppb) | 5 | 5 | 5 | 5 | 5 | 5 |
| Hexyl iodide (ppb) | 8 | 8 | 8 | 8 | 8 | 8 |
| Potassium (ppm) | 8 | 7 | 8 | 7 | 8 | 7 |
| Fe (ppm) | 1 | 1 | 0.1 | 0.1 | 0 | 0 |
| Ni (ppm) | 1 | 1 | 0.1 | 0.1 | 0 | 0 |
| Cr (ppm) | 1 | 1 | 0.1 | 0.1 | 0 | 0 |
| Mo (ppm) | 1 | 1 | 0.1 | 0.1 | 0 | 0 |
| Mn (ppm) | 1 | 1 | 0.1 | 0.1 | 0 | 0 |
| Li (ppm) | 1 | 1 | 0.1 | 0.1 | 0 | 0 |
| AMBERLYST (ppm) | 0 | 0 | 0 | 0 | 1 | 1 |
| Acetic acid | remainder | remainder | remainder | remainder | remainder | remainder |

The configurations according to the present invention and variations or modifications thereof will be listed below as a summary of the above description.

Appendix 1: A method for producing acetic acid includes preparing an acetic acid solution. The acetic acid solution includes acetic acid in a concentration of 90 mass percent or more, acetic anhydride, and water and is in such a state that the equilibrium concentration of acetic anhydride is higher than the acetic anhydride concentration. The acetic acid solution is subjected to an acetic anhydride decreasing treatment including at least one of water concentration increasing and temperature lowering, so as to bring the acetic acid solution into such a state that the equilibrium concentration of acetic anhydride is lower than the acetic anhydride concentration.

Appendix 2: A method for producing acetic acid includes preparing an acetic acid solution. The acetic acid solution includes acetic acid in a concentration of 90 mass percent or more, acetic anhydride, and water and is in such a state that the equilibrium concentration of acetic anhydride is lower than the acetic anhydride concentration. The acetic acid solution is subjected to an acetic anhydride decreasing treatment including at least one of water concentration increasing and temperature lowering, so as to further lower the equilibrium concentration of acetic anhydride.

Appendix 3: A method for producing acetic acid includes preparing an acetic acid solution. The acetic acid solution includes acetic acid in a concentration of 90 mass percent or more, acetic anhydride, and water and is in such a state that the equilibrium concentration of acetic anhydride is lower than the acetic anhydride concentration. The acetic acid solution is subjected to an acetic anhydride decreasing treatment. The acetic anhydride decreasing treatment includes temperature rising alone or in combination with water concentration increasing, as long as the state is maintained, so as to increase the reaction rate of acetic anhydride hydrolysis.

Appendix 4: In the acetic acid production method according to any one of Appendices 1 to 3, a catalyst for promoting acetic anhydride hydrolysis may be present in the acetic acid solution during the acetic anhydride decreasing treatment.

Appendix 5: In the acetic acid production method according to Appendix 4, the catalyst may include at least one substance selected from Broensted acids, Lewis acids, corrodible metals, ion exchange resins, and sulfonic acids.

Appendix 6: In the acetic acid production method according to one of Appendices 4 and 5, the catalyst in the acetic acid solution may be present in an amount of 0.01 to 10000 ppm.

Appendix 7: In the acetic acid production method according to any one of Appendices 1 to 6, the acetic anhydride decreasing treatment may be performed so that the acetic acid solution has a water concentration of 2000 ppm or more and a temperature of 180° C. or lower.

Appendix 8: In the acetic acid production method according to any one of Appendices 1 to 6, the acetic anhydride decreasing treatment may be performed so that the acetic acid solution has a water concentration of 1000 ppm or more and a temperature of 170° C. or lower.

Appendix 9: In the acetic acid production method according to any one of Appendices 1 to 6, the acetic anhydride decreasing treatment may be performed so that the acetic acid solution has a water concentration of 500 ppm or more and a temperature of 120° C. or lower.

Appendix 10: In the acetic acid production method according to any one of Appendices 1 to 6, the acetic anhydride decreasing treatment may be performed so that the acetic acid solution has a water concentration of 200 ppm or more and a temperature of 100° C. or lower.

Appendix 11: In the acetic acid production method according to any one of Appendices 1 to 6, the acetic anhydride decreasing treatment may be performed so that the acetic acid solution has a water concentration of 80 ppm or more and a temperature of 60° C. or lower.

Appendix 12: In the acetic acid production method according to any one of Appendices 1 to 6, the acetic anhydride decreasing treatment may be performed so that the acetic acid solution has a water concentration of 40 ppm or more and a temperature of 50° C. or lower.

Appendix 13: In the acetic acid production method according to any one of Appendices 1 to 6, the acetic anhydride decreasing treatment may be performed so that the acetic acid solution has a water concentration of 12 ppm or more and a temperature of 30° C. or lower.

Appendix 14: In the acetic acid production method according to any one of Appendices 1 to 13, the residence time of the acetic acid solution after the acetic anhydride decreasing treatment may be 30 seconds or longer.

Appendix 15: In the acetic acid production method according to any one of Appendices 1 to 13, the residence time of the acetic acid solution after the acetic anhydride decreasing treatment may be 1 minute or longer.

Appendix 16: In the acetic acid production method according to any one of Appendices 1 to 13, the residence time of the acetic acid solution after the acetic anhydride decreasing treatment may be 5 minutes or longer.

Appendix 17: In the acetic acid production method according to any one of Appendices 1 to 13, the residence time of the acetic acid solution after the acetic anhydride decreasing treatment may be 10 minutes or longer.

Appendix 18: In the acetic acid production method according to any one of Appendices 1 to 13, the residence time of the acetic acid solution after the acetic anhydride decreasing treatment may be 30 minutes or longer.

Appendix 19: In the acetic acid production method according to any one of Appendices 1 to 13, the residence time of the acetic acid solution after the acetic anhydride decreasing treatment may be 60 minutes or longer.

Appendix 20: In the acetic acid production method according to any one of Appendices 1 to 13, the residence time of the acetic acid solution after the acetic anhydride decreasing treatment may be 900 minutes or longer.

Appendix 21: In the acetic acid production method according to any one of Appendices 1 to 13, the residence time of the acetic acid solution after the acetic anhydride decreasing treatment may be 1300 minutes or longer.

Appendix 22: In the acetic acid production method according to any one of Appendices 1 to 13, the residence time of the acetic acid solution after the acetic anhydride decreasing treatment may be 1400 minutes or longer.

Appendix 23: In the acetic acid production method according to any one of Appendices 1 to 13, the residence time of the acetic acid solution after the acetic anhydride decreasing treatment may be 2800 minutes or longer.

Appendix 24: The acetic acid production method according to any one of Appendices 1 to 23 may be performed with acetic acid production equipment which includes a reactor, a first distillation column, a second distillation column, and a third distillation column. The method may includes a reaction step, a first distillation step, a second distillation step, and a third distillation step. In the reaction step, a material mixture containing methanol and carbon monoxide is subjected to a methanol carbonylation reaction in the reactor to form acetic acid. In the first distillation step, a crude acetic acid stream containing acetic acid formed in the reaction step is subjected to distillation in the first distillation column to give a first acetic acid stream, where the first acetic acid stream is enriched with acetic acid as compared with the crude acetic acid stream. In the second distillation step, the first acetic acid stream is subjected to distillation in the second distillation column to give a second acetic acid stream, where the second acetic acid stream is enriched with acetic acid as compared with the first acetic acid stream. In the third distillation step, the second acetic acid stream is subjected to distillation in the third distillation column to give a third acetic acid stream, where the third acetic acid stream is enriched with acetic acid as compared with the second acetic acid stream. In the method, the acetic anhydride decreasing treatment may be performed on an acetic acid stream in or downstream from the second distillation column in the acetic acid production equipment.

REFERENCE SIGNS LIST

X acetic acid production equipment
1 reactor
2 evaporator
3 distillation column (first distillation column)
4 decanter
5 distillation column (second distillation column)
6 distillation column (third distillation column)
7 ion exchange resin column
8 scrubber system

The invention claimed is:

1. A method for producing acetic acid using acetic acid production equipment comprising a reactor and a distillation column, the method comprising:
carbonylating methanol in a material mixture comprising methanol and carbon monoxide in the reactor to form acetic acid;
distilling a crude acetic acid stream comprising the formed acetic acid in a low-boiling component removing column to give a first acetic acid stream, the first acetic acid stream being enriched with acetic acid as compared with the crude acetic acid stream; and
distilling the first acetic acid stream in a dehydration column to give a second acetic acid stream enriched with acetic acid as compared with the first acetic acid stream;

distilling the second acetic acid stream in a high-boiling component removing column to give a third acetic acid stream enriched with acetic acid as compared with the second acetic acid stream;

preparing an acetic acid solution from the acetic acid stream present in or downstream from the dehydration column comprising:

acetic acid in a concentration of 90 mass percent or more;

acetic anhydride; and water, the acetic acid solution being in such a state that an equilibrium concentration of acetic anhydride is higher than an acetic anhydride concentration; and subjecting the acetic acid solution to an acetic anhydride decreasing treatment comprising at least one of water concentration increasing and temperature lowering, to bring the acetic acid solution into such a state that the equilibrium concentration of acetic anhydride is lower than the acetic anhydride concentration, wherein at least one of the following acetic anhydride decreasing treatments is performed:

(i) the acetic anhydride decreasing treatment performed on the acetic acid solution being distilled in the distillation column;

(ii) the acetic anhydride decreasing treatment performed on an acetic acid solution passing through a line between the dehydration column and the high-boiling component removing distillation column;

(iii) the acetic anhydride decreasing treatment performed on an acetic acid solution passing through an inlet line to an ion exchange resin column and/or an outlet line from the ion exchange resin column, where the method for producing acetic acid further comprises passing the acetic acid stream through the interior of the ion exchange resin column packed with an ion exchange resin to adsorb impurities in the acetic acid stream for removal; and (iv) the acetic anhydride decreasing treatment performed on an acetic acid solution passing through an inlet line to a product tank which stores an acetic acid stream; and wherein the acetic acid solution in the acetic anhydride decreasing treatment is controlled to have any one of the following:

a water concentration of 2000 ppm or more and a temperature of 180° C. or lower;

a water concentration of 1000 ppm or more and a temperature of 170° C. or lower;

a water concentration of 500 ppm or more and a temperature of 120° C. or lower;

a water concentration of 200 ppm or more and a temperature of 100° C. or lower;

a water concentration of 80 ppm or more and a temperature of 60° C. or lower;

a water concentration of 40 ppm or more and a temperature of 50° C. or lower; and a water concentration of 12 ppm or more and a temperature of 30° C. or lower.

2. The method according to claim 1 for producing acetic acid, wherein a catalyst capable of functionally promoting acetic anhydride hydrolysis is present in the acetic acid solution during the acetic anhydride decreasing treatment.

3. The method according to claim 2 for producing acetic acid, wherein the catalyst comprises at least one substance selected from the group consisting of Broensted acids, Lewis acids, corrodible metals, ion exchange resins, and sulfonic acids.

4. The method according to claim 2 for producing acetic acid, wherein the catalyst in the acetic acid solution is present in an amount of 0.01 to 10000 ppm.

5. The method according to claim 1 for producing acetic acid, wherein the acetic acid solution to be subjected to the acetic anhydride decreasing treatment is an acetic acid stream having an acetic acid concentration of 99.8% by mass or more passing through a line downstream from the dehydration column in the acetic acid production equipment.

6. A method for producing acetic acid using acetic acid production equipment comprising a reactor and a distillation column, the method comprising:

carbonylating methanol in a material mixture comprising methanol and carbon monoxide in the reactor to form acetic acid;

distilling a crude acetic acid stream comprising the formed acetic acid in a low-boiling component removing column to give a first acetic acid stream, the first acetic acid stream being enriched with acetic acid as compared with the crude acetic acid stream; and distilling the first acetic acid stream in a dehydration column to give a second acetic acid stream enriched with acetic acid as compared with the first acetic acid stream;

distilling the second acetic acid stream in a high-boiling component removing column to give a third acetic acid stream enriched with acetic acid as compared with the second acetic acid stream;

preparing an acetic acid solution from the acetic acid stream present in or downstream from the dehydration column comprising:

acetic acid in a concentration of 90 mass percent or more;

acetic anhydride; and water, the acetic acid solution being in such a state that an equilibrium concentration of acetic anhydride is lower than an acetic anhydride concentration; and subjecting the acetic acid solution to an acetic anhydride decreasing treatment comprising at least one of water concentration increasing and temperature lowering, to further lower the equilibrium concentration of acetic anhydride, wherein at least one of the following acetic anhydride decreasing treatments is performed:

(i) the acetic anhydride decreasing treatment performed on the acetic acid solution being distilled in the distillation column;

(ii) the acetic anhydride decreasing treatment performed on an acetic acid solution passing through a line between the dehydration column and the high-boiling component removing distillation column;

(iii) the acetic anhydride decreasing treatment performed on an acetic acid solution passing through an inlet line to an ion exchange resin column and/or an outlet line from the ion exchange resin column, where the method for producing acetic acid further comprises passing the acetic acid stream through the interior of the ion exchange resin column packed with an ion exchange resin to adsorb impurities in the acetic acid stream for removal; and (iv) the acetic anhydride decreasing treatment performed on an acetic acid solution passing through an inlet line to a product tank which stores an acetic acid stream; and wherein the acetic acid solution in the acetic anhydride decreasing treatment is controlled to have any one of the following:

a water concentration of 2000 ppm or more and a temperature of 180° C. or lower;

a water concentration of 1000 ppm or more and a temperature of 170° C. or lower;

a water concentration of 500 ppm or more and a temperature of 120° C. or lower;

a water concentration of 200 ppm or more and a temperature of 100° C. or lower;

a water concentration of 80 ppm or more and a temperature of 60° C. or lower;

a water concentration of 40 ppm or more and a temperature of 50° C. or lower; and a water concentration of 12 ppm or more and a temperature of 30° C. or lower.

7. The method according to claim 6 for producing acetic acid,
wherein a catalyst capable of functionally promoting acetic anhydride hydrolysis is present in the acetic acid solution during the acetic anhydride decreasing treatment.

8. The method according to claim 7 for producing acetic acid,
wherein the catalyst comprises at least one substance selected from the group consisting of Broensted acids, Lewis acids, corrodible metals, ion exchange resins, and sulfonic acids.

9. The method according to claim 7 for producing acetic acid,
wherein the catalyst in the acetic acid solution is present in an amount of 0.01 to 10000 ppm.

10. The method according to claim 6 for producing acetic acid,
wherein the acetic acid solution to be subjected to the acetic anhydride decreasing treatment is an acetic acid stream having an acetic acid concentration of 99.8% by mass or more passing through a line downstream from the dehydration column in the acetic acid production equipment.

11. A method for producing acetic acid using acetic acid production equipment comprising a reactor and a distillation column, the method comprising:
carbonylating methanol in a material mixture comprising methanol and carbon monoxide in the reactor to form acetic acid;
distilling a crude acetic acid stream comprising the formed acetic acid in a low-boiling component removing column to give a first acetic acid stream, the first acetic acid stream being enriched with acetic acid as compared with the crude acetic acid stream; and
distilling the first acetic acid stream in a dehydration column to give a second acetic acid stream enriched with acetic acid as compared with the first acetic acid stream;
distilling the second acetic acid stream in the high-boiling component removing column to give a third acetic acid stream enriched with acetic acid as compared with the second acetic acid stream;
preparing an acetic acid solution from the acetic acid stream present in or downstream from the dehydration column comprising:
acetic acid in a concentration of 90 mass percent or more;
acetic anhydride; and
water,
the acetic acid solution being in such a state that an equilibrium concentration of acetic anhydride is lower than an acetic anhydride concentration; and
subjecting the acetic acid solution to an acetic anhydride decreasing treatment comprising temperature rising alone or in combination with water concentration increasing, as long as the state being maintained, so as to perform acetic anhydride hydrolysis at a higher reaction rate,
wherein at least one of the following acetic anhydride decreasing treatments is performed:
(i) the acetic anhydride decreasing treatment performed on the acetic acid solution being distilled in the distillation column;
(ii) the acetic anhydride decreasing treatment performed on an acetic acid solution passing through a line between the dehydration column and the high-boiling component removing distillation column;
(iii) the acetic anhydride decreasing treatment performed on an acetic acid solution passing through an inlet line to an ion exchange resin column and/or an outlet line from the ion exchange resin column, where the method for producing acetic acid further comprises passing the acetic acid stream through the interior of the ion exchange resin column packed with an ion exchange resin to adsorb impurities in the acetic acid stream for removal; and
(iv) the acetic anhydride decreasing treatment performed on an acetic acid solution passing through an inlet line to a product tank which stores an acetic acid stream; and wherein the acetic acid solution in the acetic anhydride decreasing treatment is controlled to have any one of the following:

a water concentration of 2000 ppm or more and a temperature of 180° C. or lower;

a water concentration of 1000 ppm or more and a temperature of 170° C. or lower;

a water concentration of 500 ppm or more and a temperature of 120° C. or lower;

a water concentration of 200 ppm or more and a temperature of 100° C. or lower;

a water concentration of 80 ppm or more and a temperature of 60° C. or lower;

a water concentration of 40 ppm or more and a temperature of 50° C. or lower; and a water concentration of 12 ppm or more and a temperature of 30° C. or lower.

12. The method according to claim 11 for producing acetic acid,
wherein a catalyst capable of functionally promoting acetic anhydride hydrolysis is present in the acetic acid solution during the acetic anhydride decreasing treatment.

13. The method according to claim 12 for producing acetic acid,
wherein the catalyst comprises at least one substance selected from the group consisting of Broensted acids, Lewis acids, corrodible metals, ion exchange resins, and sulfonic acids.

14. The method according to claim 12 for producing acetic acid,
wherein the catalyst in the acetic acid solution is present in an amount of 0.01 to 10000 ppm.

15. The method according to claim 11 for producing acetic acid,
wherein the acetic acid solution to be subjected to the acetic anhydride decreasing treatment is an acetic acid stream having an acetic acid concentration of 99.8% by mass or more passing through a line downstream from the dehydration column in the acetic acid production equipment.

16. The method according to claim 1 for producing acetic acid, satisfying at least one of the following conditions:
a) a water concentration in the reaction mixture in the reactor being 0.1 to 15 mass percent of the entire liquid phase in the reaction mixture;
b) an acetic acid concentration in the reaction mixture in the reactor being 50 to 90 mass percent of the entire liquid phase in the reaction mixture; and
c) an acetic anhydride concentration in the reaction mixture in the reactor being 0 to 5000 ppm of the entire liquid phase in the reaction mixture.

17. The method according to claim 6 for producing acetic acid, satisfying at least one of the following conditions:
a) a water concentration in the reaction mixture in the reactor being 0.1 to 15 mass percent of the entire liquid phase in the reaction mixture;
b) an acetic acid concentration in the reaction mixture in the reactor being 50 to 90 mass percent of the entire liquid phase in the reaction mixture; and
c) an acetic anhydride concentration in the reaction mixture in the reactor being 0 to 5000 ppm of the entire liquid phase in the reaction mixture.

18. The method according to claim 11 for producing acetic acid, satisfying at least one of the following conditions:
a) a water concentration in the reaction mixture in the reactor being 0.1 to 15 mass percent of the entire liquid phase in the reaction mixture;
b) an acetic acid concentration in the reaction mixture in the reactor being 50 to 90 mass percent of the entire liquid phase in the reaction mixture; and
c) an acetic anhydride concentration in the reaction mixture in the reactor being 0 to 5000 ppm of the entire liquid phase in the reaction mixture.

* * * * *